US012753412B2

(12) United States Patent
Marson et al.

(10) Patent No.: US 12,753,412 B2

(45) Date of Patent: Oct. 6, 2026

(54) COMPOSITIONS AND METHODS FOR MODIFYING A TARGET NUCLEIC ACID

(71) Applicants: THE REGENTS OF THE UNIVERSITY OF CALIFORNIA, Oakland, CA (US); The J. David Gladstone Institutes, A Testamentary Trust Established Under the Will of J. David Gladstone, San Francisco, CA (US)

(72) Inventors: Alexander Marson, San Francisco, CA (US); Brian Shy, San Francisco, CA (US); Justin Eyquem, San Francisco, CA (US); Vivasvan Vykunta, San Francisco, CA (US)

(73) Assignees: The Regents of the University of California, Oakland, CA (US); The J. David Gladstone Institutes, A Testamentary Trust Established Under the Will of J. David Gladstone, San Francisco, CA (US)

(*) Notice: Subject to any disclaimer, the term of this patent is extended or adjusted under 35 U.S.C. 154(b) by 824 days.

(21) Appl. No.: 17/911,387

(22) PCT Filed: Mar. 12, 2021

(86) PCT No.: PCT/US2021/022102

§ 371 (c)(1),
(2) Date: Sep. 13, 2022

(87) PCT Pub. No.: WO2021/183884

PCT Pub. Date: Sep. 16, 2021

(65) Prior Publication Data

US 2023/0112075 A1 Apr. 13, 2023

Related U.S. Application Data

(60) Provisional application No. 62/989,505, filed on Mar. 13, 2020.

(51) Int. Cl.

| | |
|---|---|
| ***A61K 40/31*** | (2025.01) |
| ***A61K 40/11*** | (2025.01) |
| ***A61K 40/42*** | (2025.01) |
| ***C07K 14/705*** | (2006.01) |
| ***C12N 9/22*** | (2006.01) |
| ***C12N 15/113*** | (2010.01) |
| ***C12N 15/86*** | (2006.01) |

(52) U.S. Cl.

CPC .......... *C12N 15/1138* (2013.01); *A61K 40/11* (2025.01); *A61K 40/31* (2025.01); *A61K 40/4215* (2025.01); *C07K 14/7051* (2013.01); *C12N 9/22* (2013.01); *C12N 2310/20* (2017.05)

(58) Field of Classification Search

CPC ........ A61K 40/11; A61K 40/31; A61K 40/42; C12N 9/22; C12N 9/222; C12N 15/86; C12N 2310/22

See application file for complete search history.

(56) References Cited

U.S. PATENT DOCUMENTS

| | | | |
|---|---|---|---|
| 2005/0272080 A1 | 12/2005 | Palma et al. |
| 2016/0348073 A1 | 12/2016 | Meissner et al. |
| 2019/0055297 A1 | 2/2019 | Zhao et al. |
| 2019/0062734 A1 | 2/2019 | Cotta-ramusino et al. |
| 2020/0000851 A1 | 1/2020 | Roth et al. |

FOREIGN PATENT DOCUMENTS

| | | | |
|---|---|---|---|
| CN | 109777782 A | | 5/2019 |
| JP | 2018510657 A | | 4/2018 |
| WO | 2016160721 A1 | | 10/2016 |
| WO | WO 16/160721 | * | 10/2016 |
| WO | 2019097305 A2 | | 5/2019 |

OTHER PUBLICATIONS

Eyquem et al, Targeting a CAR to the TRAC locus with CRISPR/Cas9 enhances tumour rejection, Nature 543: 113-117 (19 pages total), doi: 10.1038/nature21405; Mar. 2, 2017.*
GenBank M94081, human TCR alpha gene, TCRdelta region, Jul. 24, 2016.*
GenBank HM852952, anti-CD19 chimeric antigen receptor, FMC63-28Z, Jun. 11, 2012.*
GenBank MK027463, synthetic construct comprising 2A self-cleaving peptide, 2018.*
PCT/US2021/022102 , "International Search Report and Written Opinion", Jul. 19, 2021, 11 pages.
EP21767869.7 , "Partial Supplementary European Search Report", Mar. 18, 2024, 23 pages.
Meissner , et al., "Human TCRA Genome Modification Specific gRNA, SEQ:9759", EBI Accession No. GSN: BDG93261, XP093135035, Dec. 1, 2016, 1 page.
Meissner , et al., "Human TCRA Genome Modification Specific gRNA, SEQ:9770", EBI Accession No. GSN: BDG93272, XP093135038, Dec. 1, 2016, 1 page.
Nguyen , et al., "Polymer-stabilized Cas9 Nanoparticles and Modified Repair Templates Increase Genome Editing Efficiency", Nature Biotechnology, vol. 38 No. 1, Jan. 2020, pp. 44-49.
Nguyen , et al., "Supplementary Online Data of Polymer-Stabilized Cas9 Nanoparticles and Modified Repair Templates Increase Genome Editing Efficiency", Nature biotechnology, Jan. 2020, 35 pages.
PCT/US2021/022102 , "International Preliminary Report on Patentability", Sep. 22, 2022, 8 pages.
Nguyen et al., "Polymer-Stabilized Cas9 Nanoparticles and Modified Repair Templates Increase Genome Editing Efficiency", Nature Biotechnology, vol. 38, No. 1, Dec. 9, 2019, pp. 44-49.

* cited by examiner

*Primary Examiner* — Kevin K Hill

(74) *Attorney, Agent, or Firm* — Kilpatrick Townsend & Stockton LLP

(57) ABSTRACT

The disclosure provides compositions and methods for for modifying an endogenous cell surface protein (e.g., an endogenous TCR) in a cell (e.g., a T cell) with a CAR or an exogenous protein (e.g., an exogenous intracellular or cell surface protein (e.g., an exogenous TCR)).

7 Claims, 24 Drawing Sheets

Specification includes a Sequence Listing.

B

SEQUENCE LISTING

<160> NUMBER OF SEQ ID NOS: 52

<210> SEQ ID NO 1
<211> LENGTH: 1532
<212> TYPE: DNA
<213> ORGANISM: Homo sapiens

<400> SEQUENCE: 1
ctcactagca ctctatcacg gccatattct ggcagggtca gtggctccaa ctaacatttg 60
tttggtactt tacagtttat taaatagatg tttatatgga gaagctctca tttctttctc 120
agaagagcct ggctaggaag gtggatgagg caccatattc attttgcagg tgaaattcct 180
gagatgtaag gagctgctgt gacttgctca aggccttata tcgagtaaac ggtagtgctg 240
gggcttagac gcaggtgttc tgatttatag ttcaaaacct ctatcaatga gagagcaatc 300
tcctggtaat gtgatagatt tcccaactta atgccaacat accataaacc tcccattctg 360
ctaatgccca gcctaagttg gggagaccac tccagattcc aagatgtaca gtttgctttg 420
ctgggccttt ttcccatgcc tgcctttact ctgccagagt tatattgctg gggttttgaa 480
gaagatccta ttaaataaaa gaataagcag tattattaag tagccctgca tttcaggttt 540
ccttgagtgg caggccaggc ctggccgtga acgttcactg aaatcatggc ctcttggcca 600
agattgatag cttgtgcctg tccctgagtc ccagtccatc acgagcagct ggtttctaag 660
atgctatttc ccgtataaag catgagaccg tgacttgcca gccccacaga gccccgccct 720
tgtccatcac tggcatctgg actccagcct gggttggggc aaagagggaa atgagatcat 780
gtcctaaccc tgatcctctt gtcccacaga tatccagaac cctgaccctg ccgtgtacca 840
gctgagagac tctaaatcca gtgacaagtc tgtctgccta ttcaccgatt ttgattctca 900
aacaaatgtg tcacaaagta aggattctga tgtgtatatc acagacaaaa ctgtgctaga 960
catgaggtct atggacttca agagcaacag tgctgtggcc tggagcaaca aatctgactt 1020
tgcatgtgca aacgccttca acaacagcat tattccagaa gacaccttct tccccagccc 1080
aggtaagggc agctttggtg ccttcgcagg ctgtttcctt gcttcaggaa tggccaggtt 1140
ctgcccagag ctctggtcaa tgatgtctaa aactcctctg attggtggtc tcggccttat 1200
ccattgccac caaaaccctc tttttactaa gaaacagtga gccttgttct ggcagtccag 1260
agaatgacac gggaaaaaag cagatgaaga gaaggtggca ggagagggca cgtggcccag 1320
cctcagtctc tccaactgag ttcctgcctg cctgcctttg ctcagactgt ttgcccctta 1380
ctgctcttct aggcctcatt ctaagcccct tctccaagtt gcctctcctt atttctccct 1440
gtctgccaaa aaatctttcc cagctcacta agtcagtctc acgcagtcac tcattaaccc 1500
accaatcact gattgtgccg gcacatgaat ac 1532

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
tcagggttct ggatatctgt 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ctggatatct gtgggacaag 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
atctgtggga caagaggatc 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tctgtgggac aagaggatca 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
gggacaagag gatcagggtt 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
tctttgcccc aacccaggct 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
ctttgcccca acccaggctg 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
tggagtccag atgccagtga 20

<210> SEQ ID NO 10
<211> LENGTH: 2923
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
tggcggaccg gttctggata tctgtcggag ctgctgtgac ttgctcaagg ccttatatcg     60
agtaaacggt agtgctgggg cttagacgca ggtgttctga tttatagttc aaaacctcta    120
tcaatgagag agcaatctcc tggtaatgtg atagatttcc caacttaatg ccaacatacc    180
ataaacctcc cattctgcta atgcccagcc taagttgggg agaccactcc agattccaag    240
atgtacagtt tgctttgctg ggcctttttc ccatgcctgc ctttactctg ccagagttat    300
attgctgggg ttttgaagaa gatcctatta aataaaagaa taagcagtat tattaagtag    360
ccctgcattt caggtttcct tgagtggcag gccaggcctg gccgtgaacg ttcactgaaa    420
tcatggcctc ttggccaaga ttgatagctt gtgcctgtcc ctgagtccca gtccatcacg    480
agcagctggt ttctaagatg ctatttcccg tataaagcat gagaccgtga cttgccagcc    540
ccacagagcc ccgccccttgt ccatcactgg catctggact ccagcctggg ttggggcaaa    600
gagggaaatg agatcatgtc ctaaccctgg aattggatcc tcttgtctta cagatggatc    660
tggagcaaca aacttctcac tactcaaaca agcaggtgac gtggaggaga atcccggccc    720
catggcactt ccagtaactg cgctgctgct cccgctcgca ctcctgctgc atgcggcccg    780
accagaacag aagcttatct ctgaagagga tcttcaggtc caactcgttc agtccggcgc    840
ggaagtaaaa aaacctggag cgtcagttaa agtatcctgt aaggcgagtg gatattcatt    900
tcccgattat tacattaatt gggtgcgaca agcgcctggt cagggtcttg aatggatggg    960
atggatatac ttcgcgtctg ggaatagtga atacaatcag aaatttaccg gcagggtgac   1020
gatgacgcga gacacctcca ttaatactgc ctatatggaa ctcagctctc tcacttcaga   1080
ggacacagcc gtctacttct gtgcctccct ttatgattac gattggtatt ttgacgtgtg   1140
gggtcaagga actatggtta ctgtgtctag cgggggaggt ggctcaggtg ggggaggttc   1200
aggaggaggc gggtccgaca tcgtgatgac acaaaccccct ctgagcctga gcgttacgcc   1260
agggcaacca gcctccattt catgcaagtc cagccagtca ctcgtgcatt caaatggaaa   1320
cacctatctg cactggtatc ttcaaaaacc aggtcagtca ccccagttgt tgatatacaa   1380
agttagtaat cgcttctccg gagtacccga tcggttcagc gggtctggtt cagggacgga   1440
tttcaccttg aaaattagcc gagttgaggc tgaagatgtg ggaatttact attgcagtca   1500
gagcagcatt taccctgga cgttcgggca gggcaccaag ttggaaatta aggcggccgc   1560
aattgaagtt atgtatcctc ctccttacct agacaatgag aagagcaatg gaaccattat   1620
ccatgtgaaa gggaaacacc tttgtccaag tcccctattt cccggacctt ctaagccctt   1680
ttgggtgctg gtggtggttg gtggagtcct ggcttgctat agcttgctag taacagtggc   1740
ctttattatt ttctgggtga ggagtaagag gagcaggctc ctgcacagtg actacatgaa   1800
catgactccc cgccgccccg ggcccacccg caagcattac cagccctatg ccccaccacg   1860
cgacttcgca gcctatcgct ccagagtgaa gttcagcagg agcgcagacg cccccgcgta   1920
ccagcagggc cagaaccagc tctataacga gctcaatcta ggacgaagag aggagtacga   1980
tgttttggac aagagacgtg gccgggaccc tgagatgggg ggaaagccga gaaggaagaa   2040
ccctcaggaa ggcctgtaca atgaactgca gaaagataag atggcggagg cctacagtga   2100
gattgggatg aaaggcgagc gccggagggg caaggggcac gatggccttt accagggtct   2160
cagtacagcc accaaggaca cctacgacgc ccttcacatg caggccctgc cccctcgcgg   2220
aagcggagct actaacttca gcctgctgaa gcaggctgga gacgtggagg agaaccctgg   2280
acccaatatc cagaaccctg accctgccgt gtaccagctg agagactcta aatccagtga   2340
```

caagtctgtc tgcctattca ccgattttga ttctcaaaca aatgtgtcac aaagtaagga 2400
ttctgatgtg tatatcacag acaaaactgt gctagacatg aggtctatgg acttcaagag 2460
caacagtgct gtggcctgga gcaacaaatc tgactttgca tgtgcaaacg ccttcaacaa 2520
cagcattatt ccagaagaca ccttcttccc cagcccaggt aagggcagct ttggtgcctt 2580
cgcaggctgt ttccttgctt caggaatggc caggttctgc ccagagctct ggtcaatgat 2640
gtctaaaact cctctgattg gtggtctcgg ccttatccat tgccaccaaa accctctttt 2700
tactaagaaa cagtgagcct tgttctggca gtccagagaa tgacacggga aaaaagcaga 2760
tgaagagaag gtggcaggag agggcacgtg gcccagcctc agtctctcca actgagttcc 2820
tgcctgcctg cctttgctca gactgtttgc cccttactgc tcttctaggc ctcattctaa 2880
gccccttctc caagtcctac agatatccag aaccgagatg gtg 2923

<210> SEQ ID NO 11
<211> LENGTH: 2923
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
tggcggacca tatctgtggg acaagcggag ctgctgtgac ttgctcaagg ccttatatcg 60
agtaaacggt agtgctgggg cttagacgca ggtgttctga tttatagttc aaaacctcta 120
tcaatgagag agcaatctcc tggtaatgtg atagatttcc caacttaatg ccaacatacc 180
ataaacctcc cattctgcta atgcccagcc taagttgggg agaccactcc agattccaag 240
atgtacagtt tgctttgctg ggcctttttc ccatgcctgc ctttactctg ccagagttat 300
attgctgggg ttttgaagaa gatcctatta aataaaagaa taagcagtat tattaagtag 360
ccctgcattt caggtttcct tgagtggcag gccaggcctg gccgtgaacg ttcactgaaa 420
tcatggcctc ttggccaaga ttgatagctt gtgcctgtcc ctgagtccca gtccatcacg 480
agcagctggt ttctaagatg ctatttcccg tataaagcat gagaccgtga cttgccagcc 540
ccacagagcc ccgcccttgt ccatcactgg catctggact ccagcctggg ttggggcaaa 600
gagggaaatg agatcatgtc ctaaccctgg aattggatcc tcttgtctta cagatggatc 660
tggagcaaca aacttctcac tactcaaaca agcaggtgac gtggaggaga atcccggccc 720
catggcactt ccagtaactg cgctgctgct cccgctcgca ctcctgctgc atgcggcccg 780
accagaacag aagcttatct ctgaagagga tcttcaggtc caactcgttc agtccggcgc 840
ggaagtaaaa aaacctggag cgtcagttaa agtatcctgt aaggcgagtg gatattcatt 900
tcccgattat tacattaatt gggtgcgaca agcgcctggt cagggtcttg aatggatggg 960
atggatatac ttcgcgtctg ggaatagtga atacaatcag aaatttaccg gcagggtgac 1020
gatgacgcga gacacctcca ttaatactgc ctatatggaa ctcagctctc tcacttcaga 1080
ggacacagcc gtctacttct gtgcctccct ttatgattac gattggtatt ttgacgtgtg 1140
gggtcaagga actatggtta ctgtgtctag cgggggaggt ggctcaggtg ggggaggttc 1200
aggaggaggc gggtccgaca tcgtgatgac acaaaacccct ctgagcctga gcgttacgcc 1260
agggcaacca gcctccattt catgcaagtc cagccagtca ctcgtgcatt caaatggaaa 1320
cacctatctg cactggtatc ttcaaaaacc aggtcagtca ccccagttgt tgatatacaa 1380
agttagtaat cgcttctccg gagtacccga tcggttcagc gggtctggtt cagggacgga 1440

```
tttcaccttg aaaattagcc gagttgaggc tgaagatgtg ggaatttact attgcagtca   1500

gagcagcatt taccccctgga cgttcgggca gggcaccaag ttggaaatta aggcggccgc   1560

aattgaagtt atgtatcctc ctccttacct agacaatgag aagagcaatg gaaccattat   1620

ccatgtgaaa gggaaacacc tttgtccaag tcccctattt cccggacctt ctaagccctt   1680

ttgggtgctg gtggtggttg gtggagtcct ggcttgctat agcttgctag taacagtggc   1740

ctttattatt ttctgggtga ggagtaagag gagcaggctc ctgcacagtg actacatgaa   1800

catgactccc cgccgccccg ggcccacccg caagcattac cagccctatg ccccaccacg   1860

cgacttcgca gcctatcgct ccagagtgaa gttcagcagg agcgcagacg cccccgcgta   1920

ccagcagggc cagaaccagc tctataacga gctcaatcta ggacgaagag aggagtacga   1980

tgttttggac aagagacgtg gccgggaccc tgagatgggg ggaaagccga gaaggaagaa   2040

ccctcaggaa ggcctgtaca atgaactgca gaaagataag atggcggagg cctacagtga   2100

gattgggatg aaaggcgagc gccggagggg caaggggcac gatggccttt accagggtct   2160

cagtacagcc accaaggaca cctacgacgc ccttcacatg caggccctgc cccctcgcgg   2220

aagcggagct actaacttca gcctgctgaa gcaggctgga gacgtggagg agaaccctgg   2280

acccaatatc cagaaccctg accctgccgt gtaccagctg agagactcta aatccagtga   2340

caagtctgtc tgcctattca ccgattttga ttctcaaaca aatgtgtcac aaagtaagga   2400

ttctgatgtg tatatcacag acaaaactgt gctagacatg aggtctatgg acttcaagag   2460

caacagtgct gtggcctgga gcaacaaatc tgactttgca tgtgcaaacg ccttcaacaa   2520

cagcattatt ccagaagaca ccttcttccc cagcccaggt aagggcagct ttggtgcctt   2580

cgcaggctgt ttccttgctt caggaatggc caggttctgc ccagagctct ggtcaatgat   2640

gtctaaaact cctctgattg gtggtctcgg ccttatccat tgccaccaaa accctctttt   2700

tactaagaaa cagtgagcct tgttctggca gtccagagaa tgacacggga aaaaagcaga   2760

tgaagagaag gtggcaggag agggcacgtg gcccagcctc agtctctcca actgagttcc   2820

tgcctgcctg cctttgctca gactgtttgc cccttactgc tcttctaggc ctcattctaa   2880

gccccttctc caagtcctct tgtcccacag atatgagatg gtg                     2923
```

```
<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Val Lys Arg Pro Ala Ala Thr Lys Lys Ala Gly Gln Ala Lys Lys
1               5                   10                  15

Lys Lys Leu Asp
            20


<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25
```

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

```
Pro Ala Ala Lys Arg Val Lys Leu Asp
1               5
```

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

```
Lys Leu Lys Ile Lys Arg Pro Val Lys
1               5
```

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

```
Pro Lys Lys Lys Arg Lys Val
1               5
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17

```
actaccgttt actcgatata                                           20
```

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18

```
tcgagtaaac ggtagtgctg                                           20
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
tagtgctggg gcttagacgc 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
atgggaggtt tatggtatgt 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
ctgggcatta gcagaatggg 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
ctaatgccca gcctaagttg 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
gtacatcttg gaatctggag 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
aactctggca gagtaaaggc 20

<210> SEQ ID NO 25
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 25

ctgccagagt tatattgctg                                              20


<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

gtgaacgttc actgaaatca                                              20


<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

agctatcaat cttggccaag                                              20


<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

caggcacaag ctatcaatct                                              20


<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

tttggcctac ggcgacggga                                              20


<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

cgataagcgt cagagcgccg                                              20


<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 31
gcatgactag accatccatg 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
gtgattgctg taaactagcc 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
tagtttacag caatcacctg 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
ggacccgata aaatacaaca 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
catagcaatt gctctatacg 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
ttcctaagtg gatcaaccca 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
ggaatgctat gagtgctgag 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
gaagctgcca caaaagctag 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
actgaacgaa catctcaaga 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
attgtttaga gctacccagc 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
aaggtctagt tctatcaccc 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
tatgtataat cctagcactg 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
gtacgtgtac gacagtgtgt 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
agcacttggg ctaagaacca 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
tcagtcctca acttaatacg 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
agaccatcct gctagcatgg 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
tctcgacttc gtgatcagcc 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
acctgtattc ccaacgacac 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49

-continued

```
tgtattccca acgacacagg                                            20


<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

gggtttctct gattagaacg                                            20


<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

catccctcac ctgatcaaga                                            20


<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

taagtcacat aagcacccag                                            20
```

COMPOSITIONS AND METHODS FOR MODIFYING A TARGET NUCLEIC ACID

CROSS-REFERENCE TO RELATED APPLICATIONS

This application in a 371 National Phase Application of International Application No. PCT/US2021/022102 filed Mar. 12, 2021, which claims priority to U.S. Provisional Application No. 62/989,505, filed Mar. 13, 2020, the disclosure of which is hereby incorporated by reference in its entirety for all purposes.

BACKGROUND OF THE DISCLOSURE

The application of clustered regularly interspaced short palindromic repeats (CRISPR) and CRISPR-associated (Cas) proteins has revolutionized molecular biology by making genome editing possible. CRISPR-mediated gene editing is a powerful and practical tool with potential for creating new scientific tools, correcting clinically relevant mutations, and engineering new cell-based immunotherapies.

BRIEF SUMMARY OF THE DISCLOSURE

In one aspect, the disclosure features a composition comprising a guide RNA (gRNA), wherein the gRNA comprises the sequence of CTGGATATCTGTGGGACAAG (SEQ ID NO:3), ATCTGTGGGACAAGAGGATC (SEQ ID NO:4), TCTGTGGGACAAGAGGATCA (SEQ ID NO:5), GGGACAAGAGGATCAGGGTT (SEQ ID NO:6), TCTTTGCCCCAACCCAGGCT (SEQ ID NO:7), CTTTGCCCCAACCCAGGCTG (SEQ ID NO:8), TGGAGTCCAGATGCCAGTGA (SEQ ID NO:9), actaccgtttactcgatata (SEQ ID NO:17), tcgagtaaacggtagtgctg (SEQ ID NO:18), tagtgctggggcttagacgc (SEQ ID NO:19), ATGGGAGGTTTATGGTATGT (SEQ ID NO:20), CTGGGCATTAGCAGAATGGG (SEQ ID NO:21), CTAATGCCCAGCCTAAGTTG (SEQ ID NO:22), GTACATCTTGGAATCTGGAG (SEQ ID NO:23), AACTCTGGCAGAGTAAAGGC (SEQ ID NO:24), CTGCCAGAGTTATATTGCTG (SEQ ID NO:25), GTGAACGTTCACTGAAATCA (SEQ ID NO:26), AGCTATCAATCTTGGCCAAG (SEQ ID NO:27), or CAGGCACAAGCTATCAATCT (SEQ ID NO:28).

In another aspect, the disclosure provides a composition comprising a guide RNA (gRNA), wherein the gRNA comprises the sequence of TTTGGCCTACGGCGACGGGA (SEQ ID NO:29), CGATAAGCGTCAGAGCGCCG (SEQ ID NO:30), GCATGACTagaccatccatg (SEQ ID NO:31), GTGATTGCTGTAAACTAGCC (SEQ ID NO:32), TAGTTTACAGCAATCACCTG (SEQ ID NO:33), ggacccgataaaatacaaca (SEQ ID NO:34), catagcaattgctctatacg (SEQ ID NO:35), TTCCTAAGTGGATCAACCCA (SEQ ID NO:36), GGAATGCTATGAGTGCTGAG (SEQ ID NO:37), GAAGCTGCCACAAAAGCTAG (SEQ ID NO:38), ACTGAACGAACATCTCAAGA (SEQ ID NO:39), or ATTGTTTAGAGCTACCCAGC (SEQ ID NO:40).

In another aspect, the disclosure provides a composition comprising a guide RNA (gRNA), wherein the gRNA comprises the sequence of aaggtctagttctatcaccc (SEQ ID NO:41), tatgtataatcctagcactg (SEQ ID NO:42), gtacgtgtacgacagtgtgt (SEQ ID NO:43), AGCacttgggctaagaacca (SEQ ID NO:44), tcagtcctcaacttaatacg (SEQ ID NO:45), agaccatcctgctagcatgg (SEQ ID NO:46), tctcgacttcgtgatcagcc (SEQ ID NO:47), acctgtattcccaacgacac (SEQ ID NO:48), tgtattcccaacgacacagg (SEQ ID NO:49), GGGTTTCTCTGATTAGAACG (SEQ ID NO:50), CATCCCTCACCTGATCAAGA (SEQ ID NO:51), or TAAGTCACATAAGCACCCAG (SEQ ID NO:52).

In some embodiments of the above aspects, the composition further comprises a homology-directed-repair template (HDRT). In some embodiments, at least one Cas protein target sequence is fused to the HDRT.

In another aspect, the disclosure provides a composition comprising a guide RNA (gRNA) and an HDRT fused to at least one Cas protein target sequence, wherein the gRNA comprises the sequence of TCAGGGTTCTGGATATCTGT (SEQ ID NO:2) and the Cas protein target sequence forms a double-stranded duplex with a complementary polynucleotide sequence.

In some embodiments, two Cas protein target sequences are fused to the HDRT. In certain embodiments, a first Cas protein target sequence is fused to the 5' terminus of the HDRT and a second Cas protein target sequence is fused to the 3' terminus of the HDRT. In certain embodiments, the Cas protein target sequence is hybridized to a complementary polynucleotide sequence to form a double-stranded duplex.

In certain embodiments, the HDRT is a single-stranded HDRT.

In some embodiments, the composition further comprises a Cas protein (e.g., Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, or a variant thereof).

In some embodiments, the Cas protein is a Cas9 nuclease.

In some embodiments, the HDRT comprises a sequence of SEQ ID NO:10 or 11.

In certain embodiments, the compositions comprises an anionic polymer. In certain embodiments, the anionic polymer comprises a polyglutamic acid (PGA), a polyaspartic acid, or a polycarboxyglutamic acid.

In another aspect, the disclosure provides a method for modifying an endogenous cell surface protein in a cell (e.g., T cell) with a CAR or an exogenous protein, comprising introducing into the cell (e.g., T cell) a composition described herein, wherein the CAR or exogenous protein is integrated into an endogenous cell surface protein genomic locus.

In some embodiments of this aspect, the endogenous cell surface protein is an endogenous TCR. In certain embodiments, the exogenous protein is an exogenous intracellular or cell surface protein. In some embodiments of this aspect, the exogenous cell surface protein is an exogenous TCR. In some embodiments, the endogenous cell surface protein genomic locus is a T cell receptor alpha constant chain (TRAC) genomic locus. In some embodiments, the endogenous cell surface protein is an endogenous beta-2 microglobulin (B2M). In certain embodiments, the endogenous cell surface protein genomic locus is a B2M genomic locus. In some embodiments, the endogenous cell surface protein is an endogenous CD4. In certain embodiments, the endogenous cell surface protein genomic locus is a CD4 genomic locus.

In some embodiments of this aspect, the introducing comprises electroporation.

In some embodiments of this aspect, the introducing comprises viral delivery. In some embodiments, the viral delivery comprises the use of a recombinant adeno-associated virus (rAAV).

In some embodiments, the method further comprises selecting for cells (e.g., T cells) that do not express the endogenous cell surface protein. In certain embodiments, the selecting comprises selecting using antibody-coated magnetic beads.

In another aspect, the disclosure provides, a method for selecting for modified cells (e.g., modified T cells) from a population of cells (e.g., a population of T cells), wherein an endogenous cell surface protein in at least some of the cells (e.g., T cells) is replaced with a chimeric antigen receptor (CAR) or an exogenous protein, comprising: (1) contacting a solution comprising the population of cells (e.g., the population of T cells) with an antibody that specifically binds the endogenous cell surface protein in the cells (e.g., T cells); and (2) separating antibody-bound cells (e.g., antibody-bound T cells) from the solution; and (3) transferring the remaining solution to a separate container, wherein following the transferring, the solution is enriched for the modified cells (e.g., modified T cells) that have the endogenous cell surface protein replaced with the CAR or the exogenous protein.

In some embodiments, the endogenous cell surface protein is an endogenous TCR.

In certain embodiments, the exogenous protein is an exogenous intracellular or cell surface protein. In some embodiments, the exogenous cell surface protein is an exogenous TCR.

In some embodiments, the endogenous cell surface protein is an endogenous B2M or an endogenous CD4.

In some embodiments, the antibody is bound to a solid support. In certain embodiments, the solid support is a magnetic bead.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1A shows TRAC locus flanking Exon 6, position of gRNA G526 and gRNA G527 target sequences, and left and right homology arms (LHA and RHA, respectively). FIGS. 1B and 1C show HDRT design for B-cell maturation antigen (BCMA)-CAR knockin using Cas protein target sequences (FIG. 1B) or rAAV-mediated delivery (FIG. 1C). P2A=self-cleaving peptide, CBS=Cas9 binding site complementary to selected gRNA, ITR=Long Terminal Repeat.

FIG. 2A shows CAR and TCR flow cytometry analysis of T cells electroporated with a scramble gRNA or G526 gRNA or G526 gRNA+TRAC-CAR rAAV. FIG. 2B shows high knockin efficiencies are reproducible with multiple donors. FIG. 2C shows that with the gRNA G527 targeting a portion of the intron, CAR+T cells can be enriched in the TCR negative population.

DETAILED DESCRIPTION OF THE DISCLOSURE

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

I. Introduction

Described herein are compositions and methods for targeted and high efficiency replacement of an endogenous cell surface protein (e.g., T cell receptor (TCR)) with a chimeric antigen receptor (CAR) or exogenous protein (e.g., an exogenous cell surface protein (e.g., an exogenous TCR)). Integration of the CAR or exogenous protein (e.g., an exogenous cell surface protein (e.g., an exogenous TCR)) (knockin) simultaneously removes expression of the endogenous cell surface protein (e.g., the endogenous TCR) (knockout). Selection for the endogenous cell surface protein-negative cells can thus enrich for cells that have both the endogenous cell surface protein-knockout and the CAR or exogenous protein knockin, each of which is desirable for therapeutic applications. In order to enrich for the modified cells by negative selection, the endogenous gene to be knocked out must encode a cell-surface protein. The exogenous gene to be knocked in can encode any exogenous protein, such as any intracellular protein or cell surface protein (e.g., a TCR). In certain embodiments, as described herein, enrichment of modified cells by negative selection provides the unique advantage in enriching for modified cells that contain an exogenous intracellular protein, as such modified cells cannot be selected through positive selection.

Figure 9A:
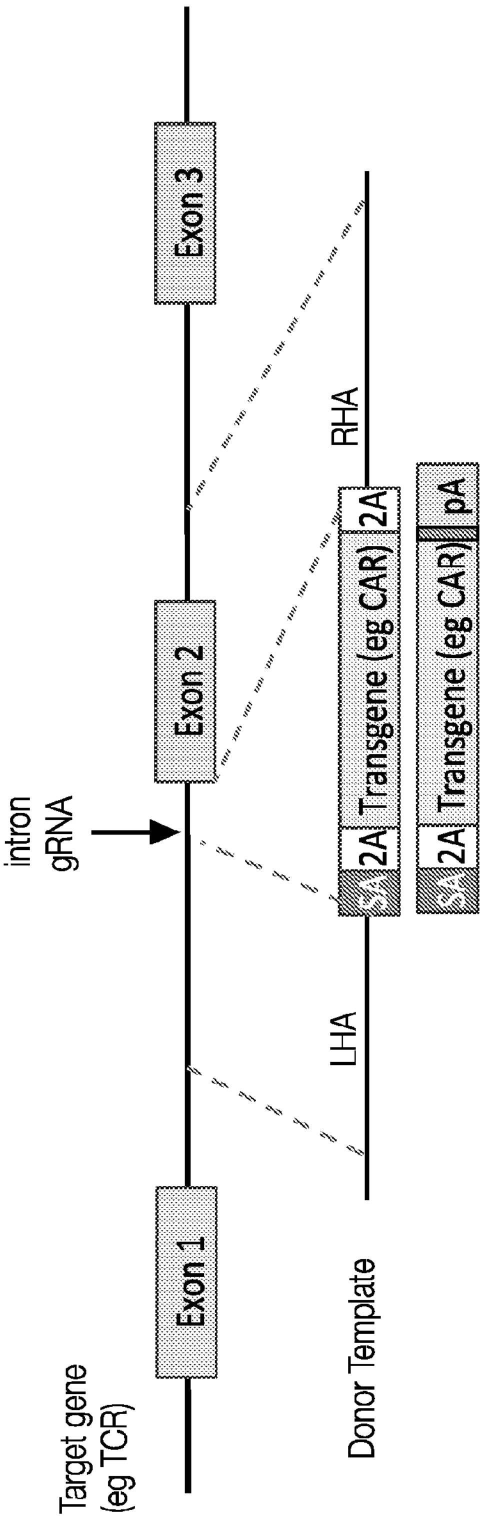
FIGS. 9A-9C show schematic representations of different intronic KI strategies. SA: Splice Acceptor, SD: Splice Donor, 2A: cleaving peptide, Red bar: Stop Codon, LHA: Left Homology Arm, RHA: Right Homology Arm.
Figure 9B:
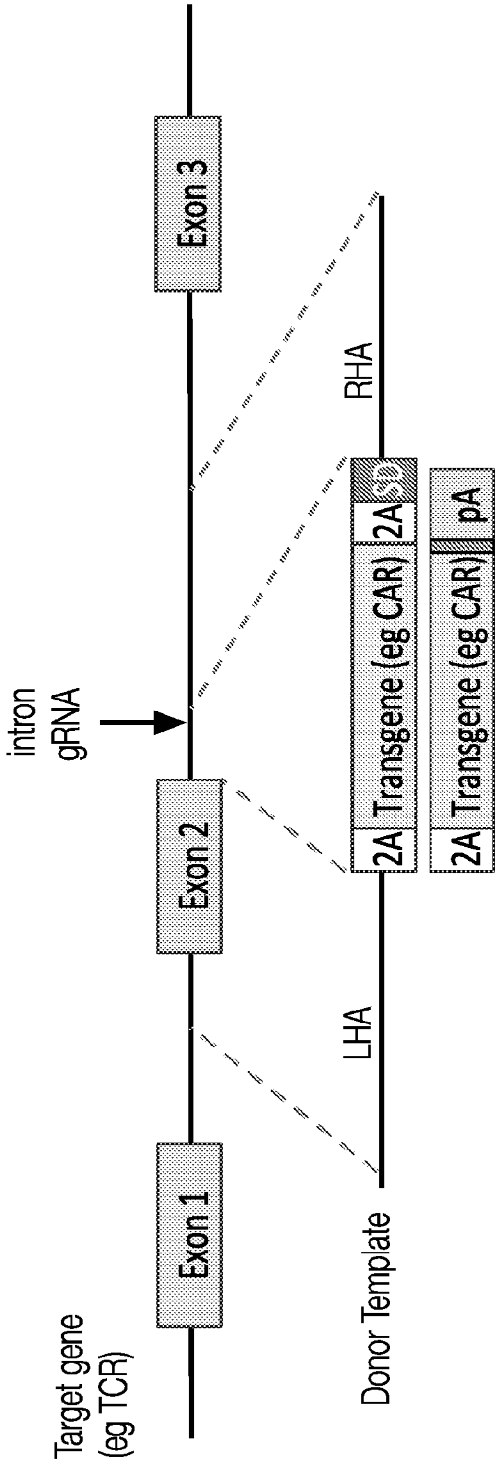
Figure 9C:
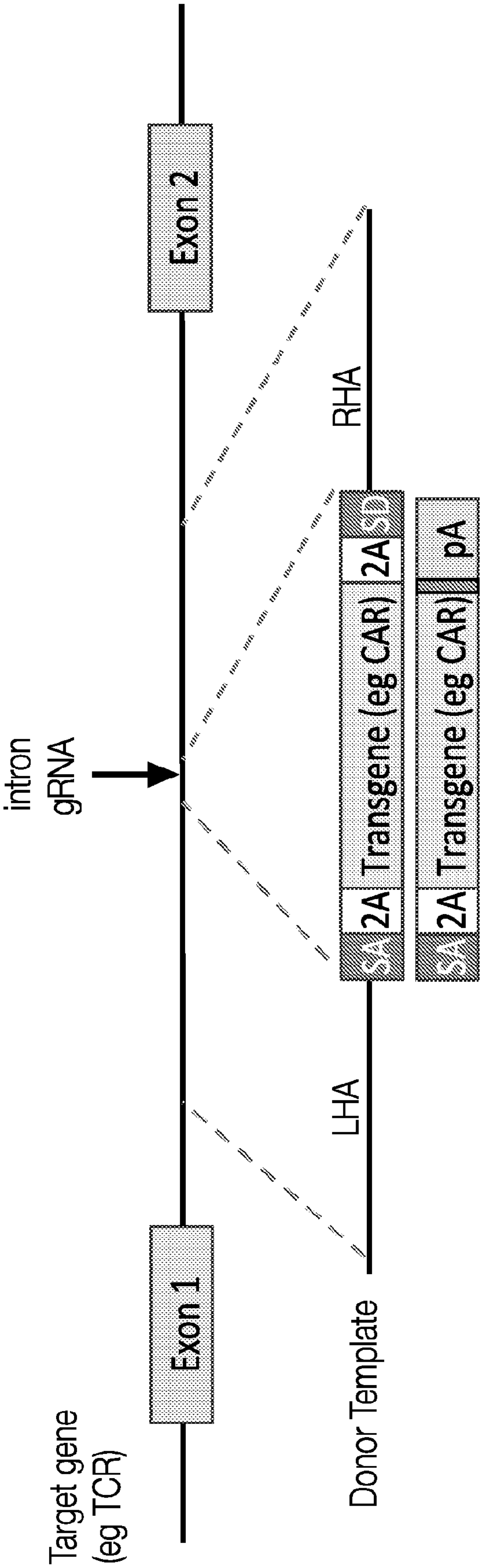

In addition to generating expression of the desired CAR or exogenous protein (e.g., an exogenous cell surface protein (e.g., an exogenous TCR)), concurrent knockout of the endogenous cell surface protein reduces potential off-target effects, opens therapies to previously excluded patients, such as those with autoimmune disease, and reduces potential for Graft-Versus-Host disease (GVHD) in the allogeneic setting. Schematic representations of different intronic KI strategies are shown in FIGS. 9A-9C. FIG. 9A illustrates an example of an intronic KI strategy close to the 5' end of an exon. The transgene's sequence is juxtaposed to the exon and a novel splice acceptor is added. FIG. 9B illustrates an example of an intronic KI strategy close to the 3' end of an exon. The transgene's sequence is juxtaposed to the exon and a novel splice donor is added. FIG. 9C illustrates an example of an intronic KI strategy in the middle of an intron, in which a splice acceptor and a splice donor add a new exon to the transcript. For the three examples shown in FIGS. 9A-9C, the top donor template constructs comprise a transgene flanked by 2A sequences to preserve the transcriptional regulation of the endogenous gene. The bottom donor template constructs terminate the translation and transcription with a stop codon and a polyadenylation sequence.

The desired genetic change is stimulated by introduction of a Cas protein (e.g., Cas9 protein) and guide RNA (gRNA) ribonucleoprotein (RNP) which introduces a double-stranded or single-stranded break at the chosen gRNA sequence within the endogenous cell surface protein locus (e.g., T cell receptor alpha constant chain (TRAC) genomic locus (FIG. 1A)). Repair of this break can proceed by either homology-directed-repair (HDR), which makes use of homologous DNA templates to direct repair outcomes, or by non-homologous-end-joining (NHEJ), which directly ligates the broken ends in an error-prone manner leading to frequent insertion or deletion of the surrounding bases (indels). The effect of NHEJ-mediated indels is dependent on the location of the gRNA target sequence. Those gRNAs targeting a coding sequence or nearby structural elements are prone to disrupting protein or mRNA expression, leading to NHEJ-mediated knockout of the targeted gene. The balance of NHEJ to HDR events is dependent on both the choice of gRNA target sequence and the availability of an HDR template (HDRT).

Figures 1A, 1B, 1C:
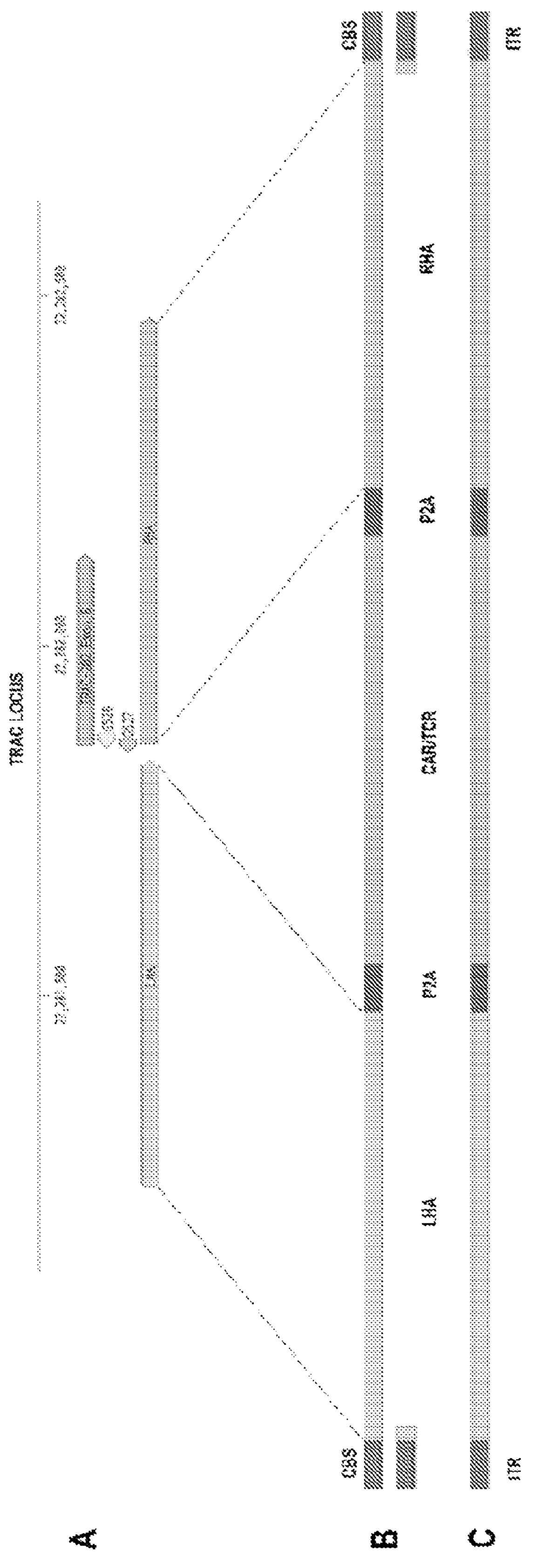
FIGS. 1A-1C: Knockin strategy for introduction of CAR or exogenous TCR at the endogenous TRAC locus.

As described herein, integration of the CAR or exogenous protein (e.g., an exogenous intracellular or cell surface protein (e.g., an exogenous TCR)) into a T cell at the gRNA target site is directed by co-delivery of an HDRT which includes a left and right homology arm having homology to sequences flanking the genomic break (LHA and RHA, respectively) and surrounding the CAR or exogenous protein (e.g., an exogenous intracellular or cell surface protein (e.g., an exogenous TCR)) insert. In some embodiments, the CAR or exogenous protein (e.g., an exogenous intracellular or cell surface protein (e.g., an exogenous TCR)) is integrated in-frame at the endogenous cell surface protein locus (e.g., TRAC locus), following a self-cleaving peptide (e.g., P2A, E2A, T2A, or F2A) (FIGS. 1B and 1C). This leads to expression of the CAR or exogenous protein (e.g., an exogenous intracellular or cell surface protein (e.g., an exogenous TCR)) insert while simultaneously interrupting expression of the endogenous cell surface protein (e.g., endogenous TCR).

Figures 2A, 2B, 2C:
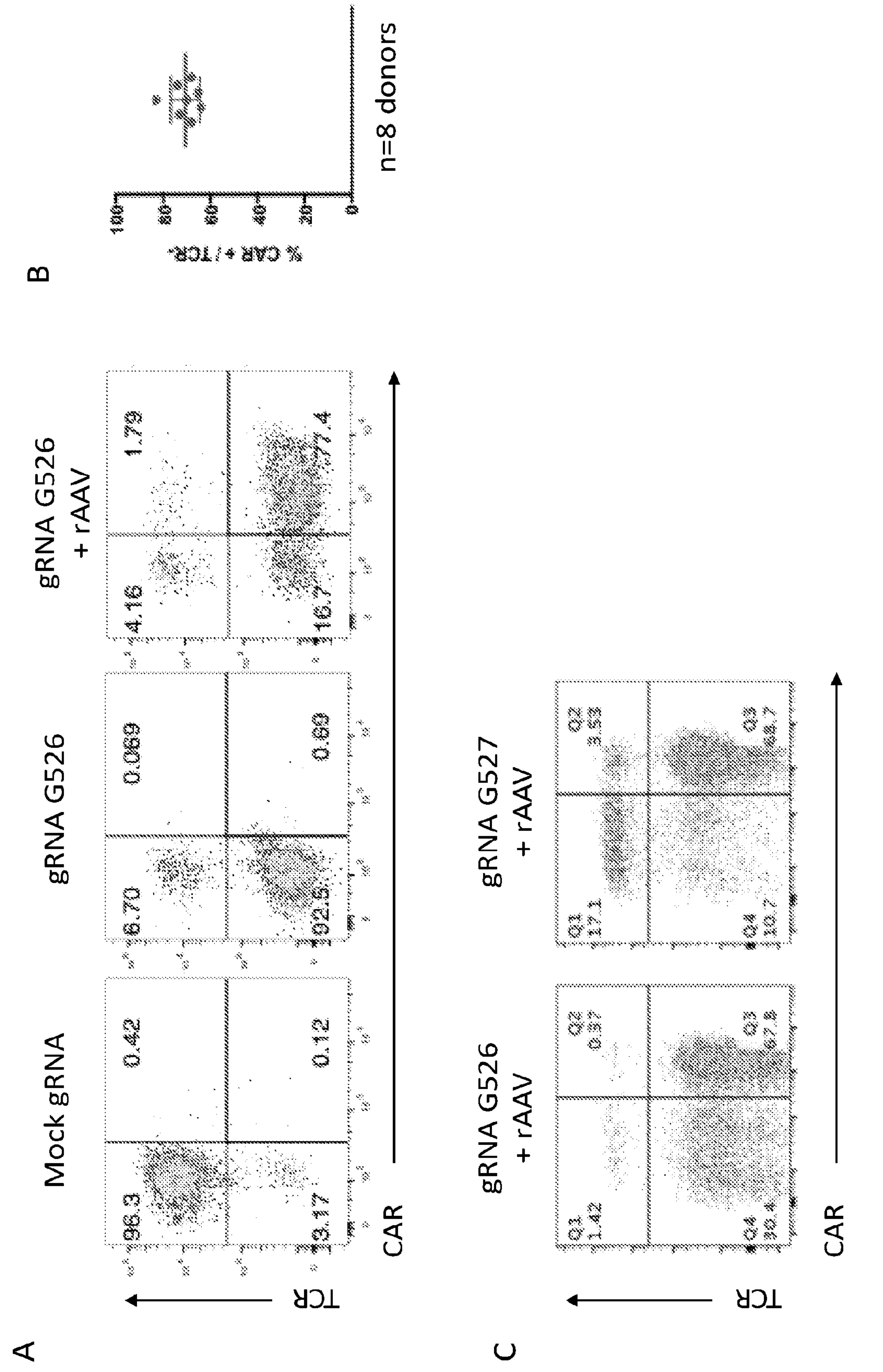
FIGS. 2A-2C: rAAV-mediated knockin.
Figure 3A:
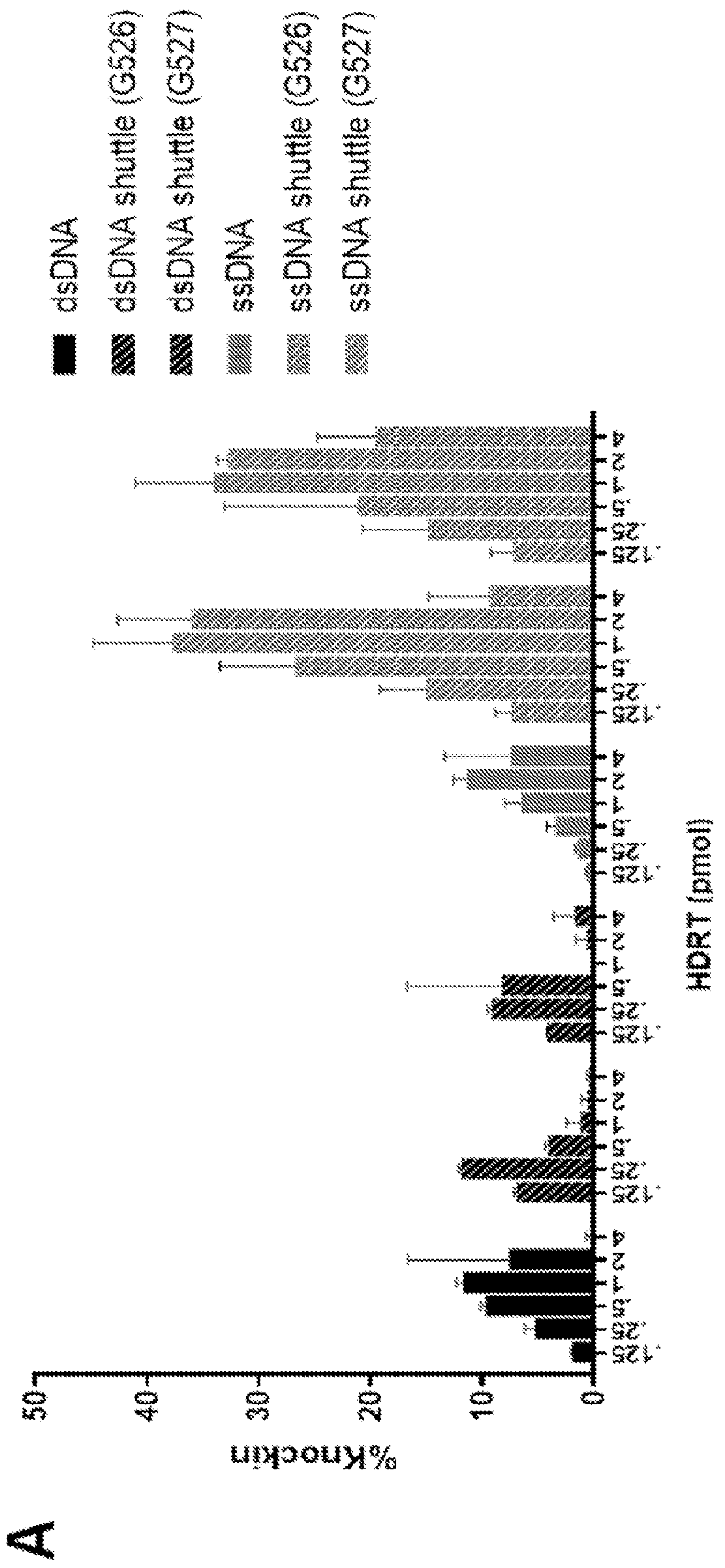
FIGS. 3A-3C: ssDNA shuttle-mediated knockin. Both gRNA G526 and gRNA G527 ssDNA shuttle variants increased the maximum knockin efficiency (FIG. 3A), increased cellular viability (FIG. 3B), and increased the total number of cells recovered with the desired genetic change (FIG. 3C).
Figure 3B:
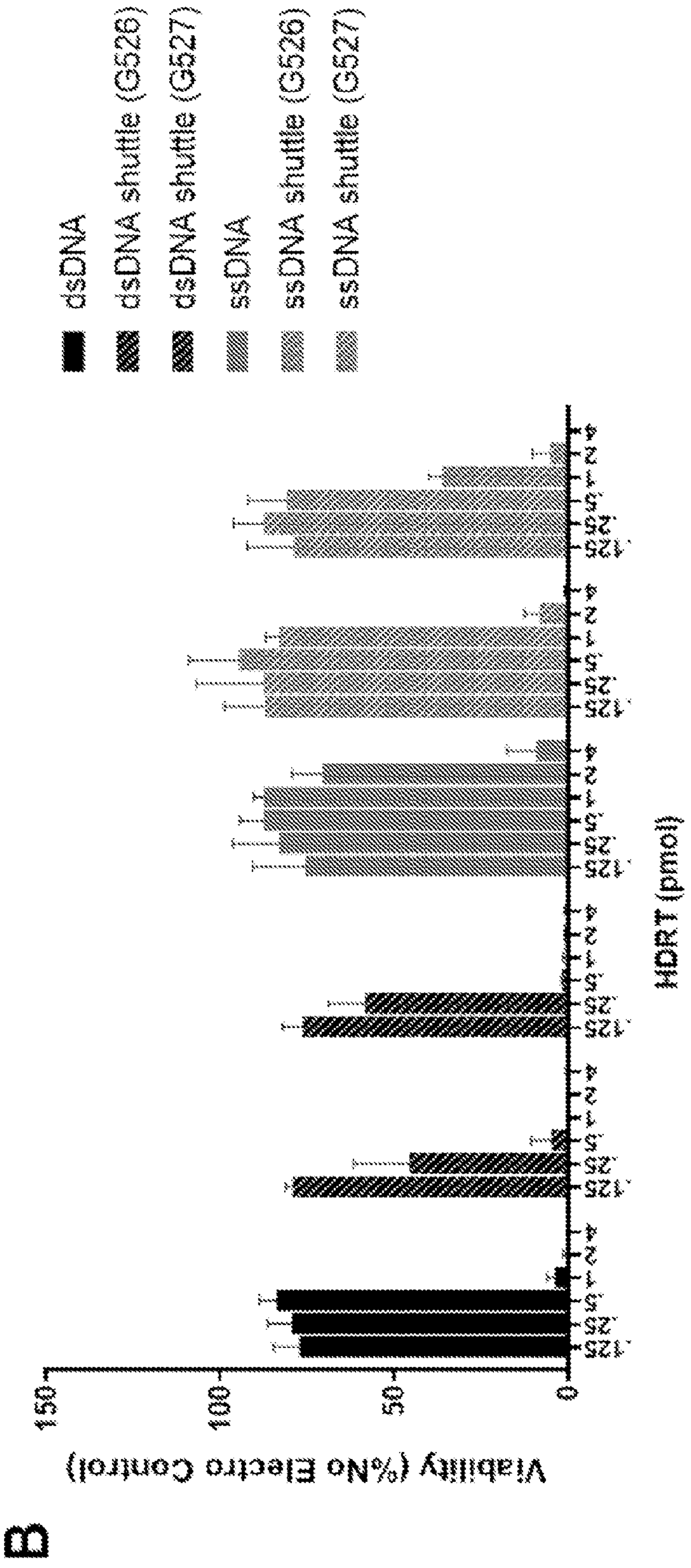
Figure 3C:
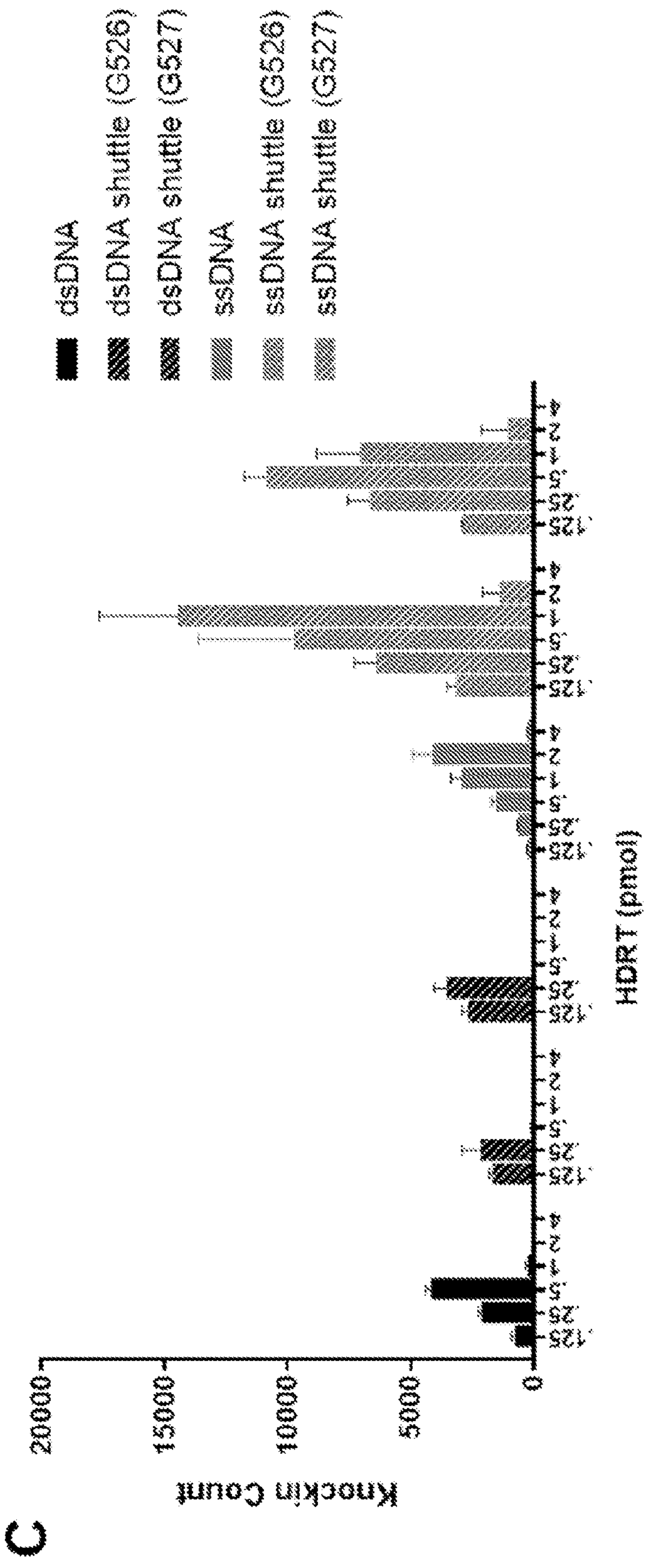

Knockin efficiency is directly correlated to nuclear concentration of the HDRT and can be increased by delivering the HDRT with either recombinant adeno-associated virus (rAAV, FIGS. 2A-2C) or ssDNA/dsDNA hybrid Cas9 shuttle (ssDNA shuttle, FIGS. 3A-3C). The latter involves generating a ssDNA HDRT, as described above, with addition of dsDNA ends including Cas protein target sequences (e.g., "shuttle sequences"). This allows the co-delivered RNP to bind directly to the HDRT, improving stability and nuclear delivery of the HDRT. As illustrated in FIGS. 3A-3C, this system significantly increases knockin efficiency while reducing cellular toxicity of the HDRT. In addition to the above, HDRT can also be deliver with linear ssDNA, linear dsDNA, plasmid and/or minicircle DNA, or viral DNA (e.g., non-integrating lenti or retrovirus genomic DNA).

Figure 4A:
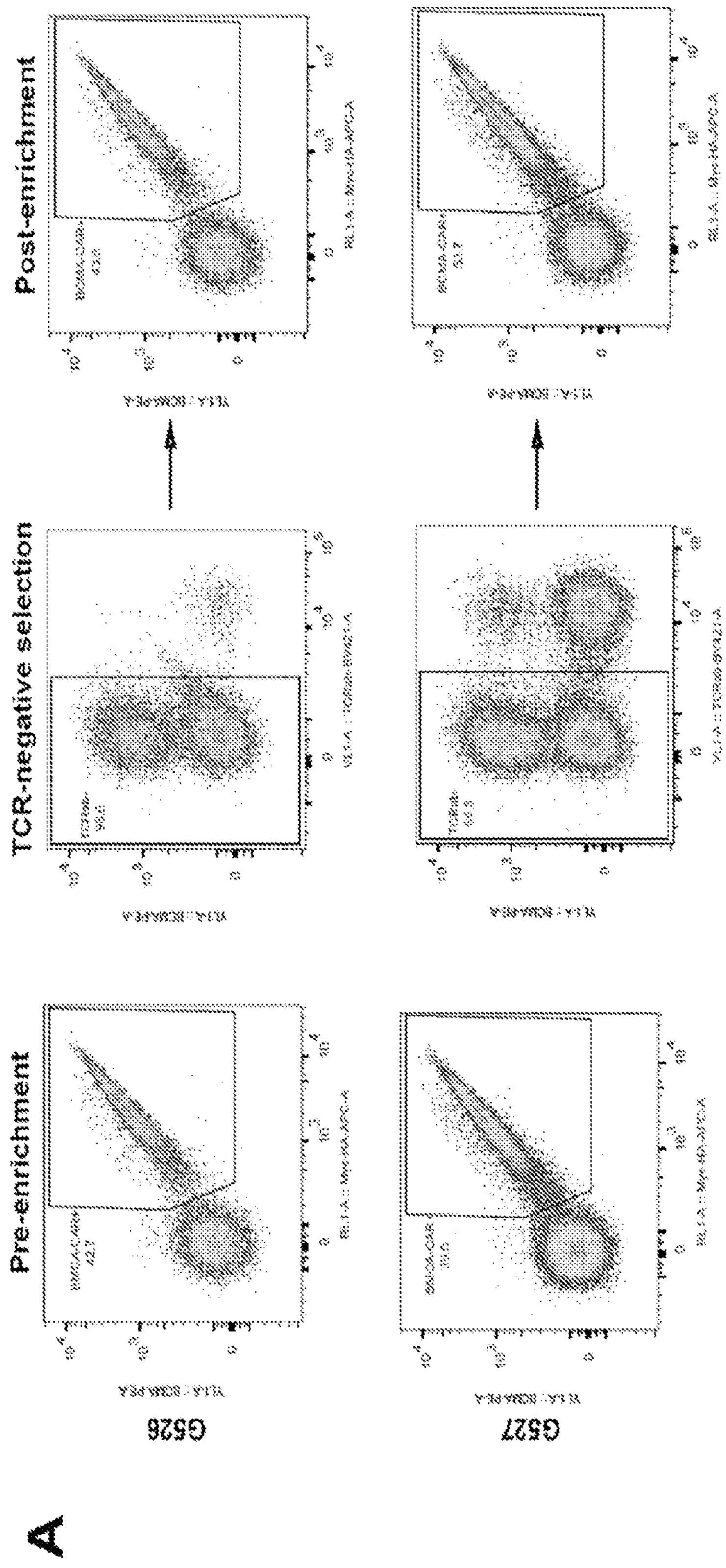
FIGS. 4A and 4B: Enrichment of knockin by TCR-negative selection. TCR-negative selection significantly enriches for cells with the desired knockin when guide G527 is used but not guide G526.
Figure 4B:
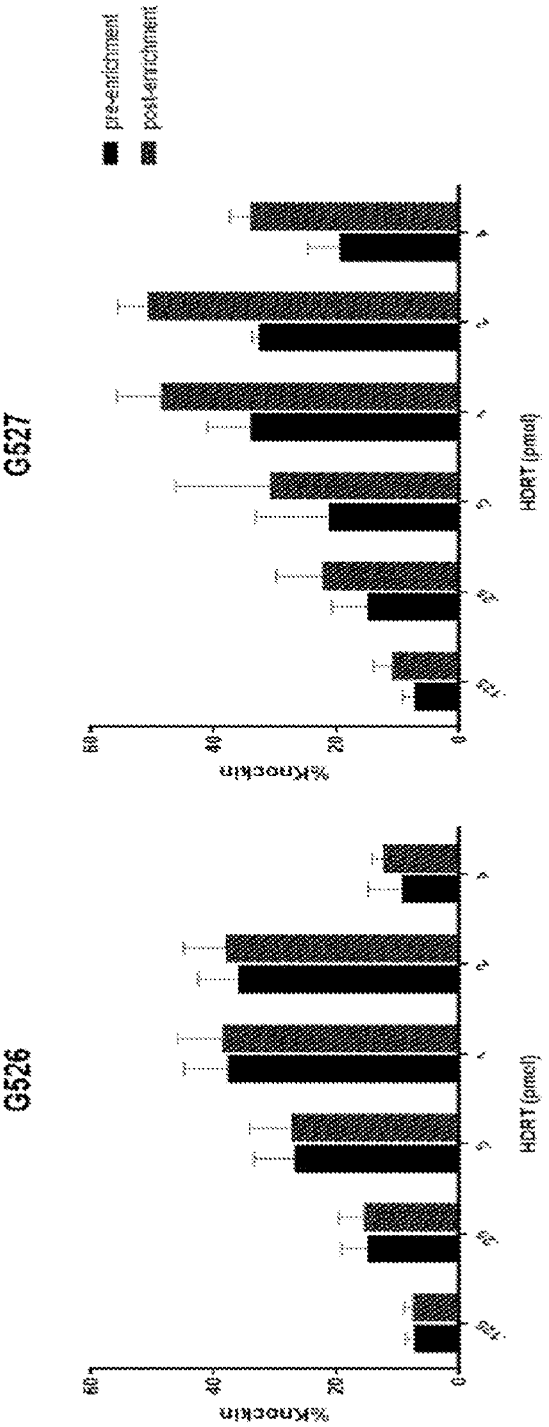

In some embodiments, a gRNA target sequence is chosen that stimulates high levels of HDR but also demonstrates low levels of NHEJ-mediated cell surface protein (e.g., TCR) disruption. Because the HDR-mediated knockin removes expression of the endogenous cell surface protein (e.g., endogenous TCR), HDR events can be enriched by selecting for endogenous cell surface protein-negative cells. This enrichment strategy can lead to a mixture of cells with HDR-mediated loss of the endogenous cell surface protein (desired outcome) and NHEJ-mediated knockouts. The lower the level of NHEJ-mediated knockout, the greater the ratio of HDR:NHEJ events within this pool, and the more this strategy will enrich for the desired knockin. In some embodiments, to enrich for the desired knockin with high ratio of HDR:NHEJ events, the selection of a gRNA target sequence has sufficient distance from the exon such that random indels would not disrupt the protein coding-sequence or nearby structural elements. FIGS. 2-4 demonstrate data from two different gRNA sequences, G526 and G527. In the absence of an HDRT, G526 disrupts nearly all protein expression while G527, which is placed further upstream in the intronic region, exhibits lower levels of protein disruption (FIGS. 4A and 4B). Combined with an HDRT, both gRNA can stimulate nearly equivalent high efficiency knockin. However, selection for the endogenous cell surface protein-negative (e.g., endogenous TCR-negative) population significantly enriches for knockin events only with G527 (FIGS. 4A and 4B).

II. Definitions

As used in this specification and the appended claims, the singular forms "a," "an," and "the" include plural reference unless the context clearly dictates otherwise.

As used herein, the "CRISPR-Cas" system refers to a class of bacterial systems for defense against foreign nucleic acid. CRISPR-Cas systems are found in a wide range of eubacterial and archaeal organisms. CRISPR-Cas systems include type I, II, and III sub-types. Wild-type type II CRISPR-Cas systems utilize an RNA-mediated nuclease, for example, Cas9 protein, in complex with guide and activating RNA (e.g., single-guide RNA or sgRNA) to recognize and cleave foreign nucleic acids, i.e., foreign nucleic acids including natural or modified nucleotides.

As used herein, the term "double-stranded duplex" refers to two regions of polynucleotides that are complementary to each other and hybridize to each other via hydrogen bonding to form a double-stranded region. In some embodiments, the two regions of complementary polynucleotides can be within the same strand polynucleotide molecule. In other embodiments, the two regions of complementary polynucleotides can be from separate strands of polynucleotide molecules.

As used herein, the term "Cas protein target sequence" refers to a nucleotide sequence that is recognized and bound by a Cas protein. A Cas protein can indirectly recognize and bind a Cas protein target sequence via a gRNA. The Cas protein binds to the gRNA, which hybridizes to the Cas protein target sequence. In some embodiments, the Cas protein target sequence is a portion of the target nucleic acid. In some embodiments, a Cas protein target sequence has between 15 and 40 (e.g., between 15 and 35, between 15 and 30, between 15 and 25, between 15 and 20, between 20 and 35, between 25 and 35, or between 30 and 35) nucleotides. In some embodiments, a Cas protein target sequence is also referred to as a shuttle sequence.

As used herein, the term "guide RNA" or "gRNA" refers to a DNA-targeting RNA that can guide a Cas protein to a target nucleic acid by hybridizing to the target nucleic acid. In some embodiments, a guide RNA can be a single-guide RNA (sgRNA), which contains a guide sequence (i.e., crRNA equivalent portion of the single-guide RNA) that targets the Cas protein to the target nucleic acid and a scaffold sequence (i.e., tracrRNA equivalent portion of the single-guide RNA) that interacts with the Cas protein. In other embodiments, a guide RNA can contain two components, a guide sequence (i.e., crRNA equivalent portion of the single-guide RNA) that targets the Cas protein to the target nucleic acid and a scaffold sequence (i.e., tracrRNA equivalent portion of the single-guide RNA) that interacts with the Cas protein. A portion of the guide sequence can hybridize to a portion of the scaffold sequence to form the two-component guide RNA.

As used herein, the term "hybridize" or "hybridization" refers to the annealing of complementary nucleic acids through hydrogen bonding interactions that occur between complementary nucleobases, nucleosides, or nucleotides. The hydrogen bonding interactions may be Watson-Crick hydrogen bonding or Hoogsteen or reverse Hoogsteen hydrogen bonding. Examples of complementary nucleobase pairs include, but are not limited to, adenine and thymine, cytosine and guanine, and adenine and uracil, which all pair through the formation of hydrogen bonds.

As used herein, the term "complementary" or "complementarity" refers to the capacity for base pairing between nucleobases, nucleosides, or nucleotides, as well as the capacity for base pairing between one polynucleotide to another polynucleotide. In some embodiments, one polynucleotide can have "complete complementarity," or be "completely complementary," to another polynucleotide, which means that when the two polynucleotides are optionally aligned, each nucleotide in one polynucleotide can engage in Watson-Crick base pairing with its corresponding nucleotide in the other polynucleotide. In other embodiments, one polynucleotide can have "partial complementarity," or be "partially complementary," to another polynucleotide, which means that when the two polynucleotides are optionally aligned, at least 60% (e.g., 65%, 70%, 75%, 80%, 85%, 90%, 95%, or 97%) but less than 100% of the nucleotides in one polynucleotide can engage in Watson-Crick base pairing with their corresponding nucleotides in the other polynucleotide. In other words, there is at least one (e.g., one, two, three, four, five, six, seven, eight, nine, or ten) mismatched nucleotide base pair when the two polynucleotides are hybridized. Pairs of nucleotides that engage in Watson-Crick base pairing includes, e.g., adenine and thymine, cytosine and guanine, and adenine and uracil, which all pair through the formation of hydrogen bonds. Examples of mismatched bases include a guanine and uracil, guanine and thymine, and adenine and cytosine pairing.

As used herein, the phrase "specifically binds" to a target refers to a binding reaction whereby an agent (e.g., an antibody) binds to the target with greater affinity, greater avidity, and/or greater duration than it binds to a structurally different molecule. In typical embodiments, the agent (e.g., antibody) has at least 5-fold, 6-fold, 7-fold, 8-fold, 9-fold, 10-fold, 20-fold, 25-fold, 50-fold, or 100-fold, or greater affinity for a target compared to an unrelated molecule when assayed under the same affinity assay conditions.

As used herein, the term "Cas protein" refers to a Clustered Regularly Interspaced Short Palindromic Repeats-associated protein or nuclease. A Cas protein can be a wild-type Cas protein or a Cas protein variant. Cas9 protein is an example of a Cas protein that belongs in the type II CRISPR-Cas system (e.g., Rath et al., *Biochimie* 117:119, 2015). Other examples of Cas proteins are described in detail further herein. A naturally-occurring Cas protein requires both a crRNA and a tracrRNA for site-specific DNA recognition and cleavage. The crRNA associates, through a region of partial complementarity, with the tracrRNA to guide the Cas protein to a region homologous to the crRNA in the target DNA called a "protospacer". A naturally-occurring Cas protein cleaves DNA to generate blunt ends at the double-strand break at sites specified by a guide sequence contained within a crRNA transcript. In some embodiments of the compositions and methods described herein, a Cas protein associates with a target gRNA or a donor gRNA to form a ribonucleoprotein (RNP) complex. In some embodiments of the compositions and methods described herein, the Cas protein has nuclease activity. In other embodiments, the Cas protein does not have nuclease activity.

As used herein, the term "Cas protein variant" refers to a Cas protein that has at least one amino acid substitution (e.g., one, two, three, four, five, six, seven, eight, nine, ten, or more amino acid substitutions) relative to the sequence of a wild-type Cas protein and/or is a truncated version or fragment of a wild-type Cas protein. In some embodiments, a Cas protein variant has at least 75% sequence identity (e.g., at least 75%, 80%, 85%, 90%, 91%, 92%, 93%, 94% 95%, 96%, 97%, 98%, 99%, or 100% sequence identity) to the sequence of a wild-type Cas protein. In some embodiments, a Cas protein variant is a fragment of a wild-type Cas protein and has at least one amino acid substitution relative to the sequence of the wild-type Cas protein. A Cas protein variant can be a Cas9 protein variant. In some embodiments, a Cas protein variant has nuclease activity. In other embodiments, a Cas protein variant does not have nuclease activity.

As used herein, the term "ribonucleoprotein complex" or "RNP complex" refers to a complex comprising a Cas protein or variant (e.g., a Cas9 protein or variant) and a gRNA.

As used herein, the term "modifying" in the context of modifying a target nucleic acid in the genome of a cell refers to inducing a change (e.g., cleavage) in the target nucleic acid. In some embodiments, the change can be a structural change in the sequence of the target nucleic acid. For example, the modifying can take the form of inserting a nucleotide sequence into the target nucleic acid. For example, an exogenous nucleotide sequence can be inserted into the target nucleic acid. The target nucleic acid can also be excised and replaced with an exogenous nucleotide sequence. In another example, the modifying can take the form of cleaving the target nucleic acid without inserting a nucleotide sequence into the target nucleic acid. For example, the target nucleic acid can be cleaved and excised. Such modifying can be performed, for example, by inducing a double stranded break within the target nucleic acid, or a pair of single stranded nicks on opposite strands and flanking the target nucleic acid. Methods for inducing single or double stranded breaks at or within a target nucleic acid include the use of a Cas protein as described herein directed to the target nucleic acid. In other embodiments, modifying a target nucleic acid includes targeting another protein to the target nucleic acid and does not include cleaving the target nucleic acid.

As used herein, the term "exogenous protein" refers to a protein that is not found in the cell or a protein that is not normally found at the targeted genomic location but otherwise present in the cell.

As used herein, the term "anionic polymer" refers to a molecule composed of multiple subunits or monomers that has an overall negative charge. Each subunit or monomer in a polymer can, independently, be an amino acid, a small organic molecule (e.g., an organic acid), a sugar molecule (e.g., a monosaccharide or a disaccharide), or a nucleotide. An anionic polymer can contain multiple amino acids, small organic molecules (e.g., organic acids), nucleotides (e.g., natural or non-natural nucleotides, or analogues thereof), or a combination thereof. An anionic polymer can be an anionic homopolymer where all subunits or monomers in the polymer are the same. An anionic polymer can be an anionic heteropolymer where the subunits and monomers in the polymer are different. An anionic polymer does not refer to a nucleic acid, such as a deoxyribonucleic acid (DNA), ribonucleic acid (RNA), that is composed entirely of nucleotides. However, an anionic polymer can include one or more nucleobases (e.g., guanosine, cytidine, adenosine, thymidine, and uridine) together with other subunits or monomers, such as amino acids and/or small organic molecules (e.g., an organic acid). In some embodiments, at least 50% (e.g., 55%, 60%, 65%, 70%, 75%, 80%, 85%, 90%, 95%, or 100%) of the subunits or monomers in the polymer are not nucleotides or do not contain nucleobases. An anionic polymer can be an anionic polypeptide or an anionic polysaccharide. An anionic polymer can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

As used herein, the term "anionic polypeptide" refers to an anionic polymer that has at least 50% (e.g., 55%, 60%, 65%, 70%, 75%, 80%, 85%, 90%, 95%, or 100%) of its subunits or monomers being amino acids, such as acidic amino acids (e.g., glutamic acids and aspartic acids), or derivatives thereof. Aside from amino acids, an anionic polypeptide can also contain small organic molecules (e.g., organic acids), sugar molecules (e.g., monosaccharides or disaccharides), or nucleotides. In some embodiments, an anionic polypeptide can be a homopolymer where all of its subunits are the same. In other embodiments, an anionic polypeptide can be a heteropolymer that contains two or more different subunits. For example, an anionic polypeptide can be polyglutamic acid (PGA) (e.g., poly-gamma-glutamic acid), polyaspartic acid, and polycarboxyglutamic acid. In another example, an anionic polypeptide can contain a mixture of glutamic acids and aspartic acids. In some embodiments, at least 50% (e.g., 55%, 60%, 65%, 70%, 75%, 80%, 85%, 90%, 95%, or 100%) of the subunits or monomers in an anionic polypeptide can be glutamic acids and/or aspartic acids. An anionic polypeptide can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

As used herein, the term "anionic polysaccharide" refers to an anionic polymer that has at least 50% (e.g., 55%, 60%, 65%, 70%, 75%, 80%, 85%, 90%, 95%, or 100%) of its subunits or monomers being sugar molecules, such as monosaccharides (e.g., fructose, galactose, and glucose) and disaccharides (e.g., hyaluronic acid, lactose, maltose, and sucrose), or derivatives thereof. Aside from sugar molecules, an anionic polysaccharide can also contain small organic molecules (e.g., organic acids), amino acids (e.g., glutamic acids or aspartic acids), or nucleotides. In some embodiments, an anionic polysaccharide can be a homopolymer where all of its subunits are the same. In other embodiments, an anionic polysaccharide can be a heteropolymer that contains two or more different subunits. For example, an anionic polysaccharide can be hyaluronic acid (HA), heparin, heparin sulfate, or glycosaminoglycan. In some embodiments, at least 50% (e.g., 55%, 60%, 65%, 70%, 75%, 80%, 85%, 90%, 95%, or 100%) of the subunits or monomers in an anionic polysaccharide can be HA. An anionic polysaccharide can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

III. Compositions and Methods for Modifying an Endogenous Cell Surface Protein In compositions and methods described herein that modify an endogenous cell surface protein in a cell with a CAR or an exogenous protein (e.g., an exogenous intracellular or cell surface protein), the location in the endogenous cell surface protein locus (e.g., T cell receptor alpha constant chain (TRAC) genomic locus) that the gRNA targets can promote a high level of HDR and low level of NHEJ, which directly ligates the cleaved ends in an error-prone manner that leads to frequent indels. In some embodiments, a gRNA targeting a coding sequence or nearby structural elements can disrupt protein or mRNA expression, which can also lead to undesired NHEJ-mediated knockout of the gene. Without being bound by any theory, having a gRNA targeting an intronic region (e.g., an intronic region in intron 5, 6, or 7 of the TRAC locus), or a portion thereof, in an endogenous cell surface protein locus (e.g., the TRAC locus) can lead to high level of HDR and low level of NHEJ. In some embodiments, a gRNA targets a region in the endogenous cell surface protein locus (e.g., the TRAC locus) that contains both an intronic region (e.g., an intronic region in intron 5, 6, or 7 of the TRAC locus) and an exonic region.

Figure 5:
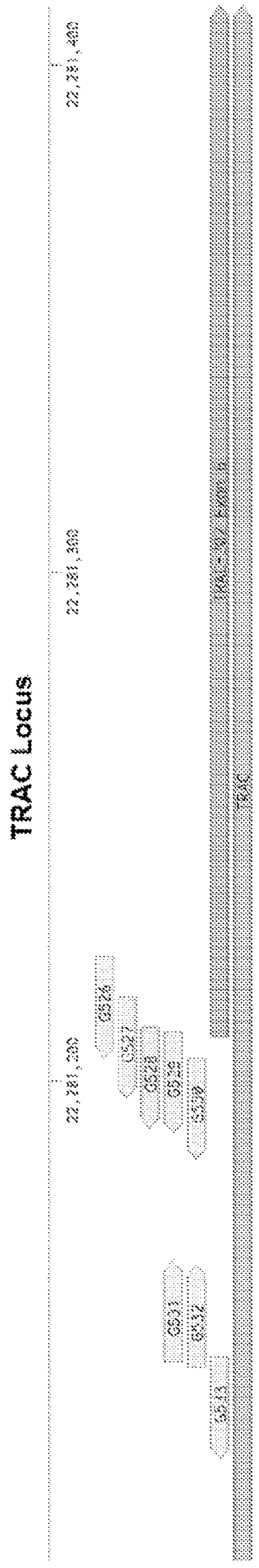
FIG. 5: Schematic representation of CRISPR/Cas9-targeted integration into the TRAC locus using gRNAs of SEQ ID NOS:2-9.
Figure 6A:
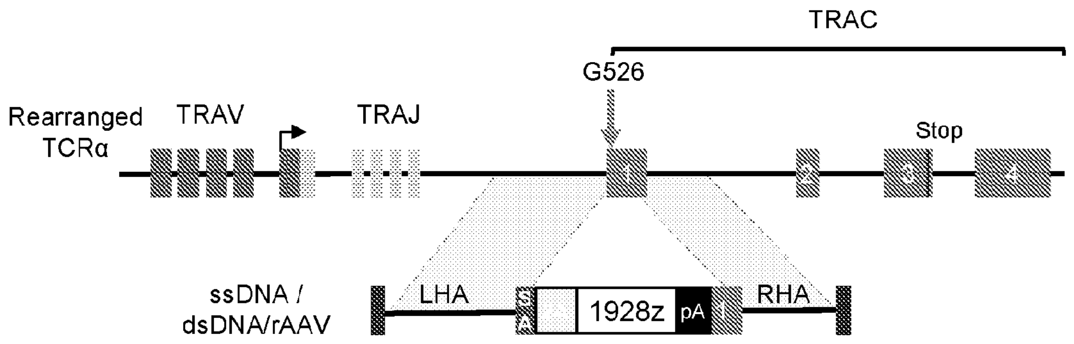
FIGS. 6A and 6B: Schematic representation of CRISPR/Cas9-targeted integration into the TRAC locus. The targeting construct contains a splice acceptor (SA), followed by a 2A cleaving peptide, coding sequence, the 1928z CAR gene and a polyA sequence, flanked by sequences homologous to the TRAC locus (LHA and RHA: left and right homology arm). Once integrated, the endogenous TCRα promoter drives CAR expression, while TRAC locus is disrupted. TRAV: TCR alpha variable region. TRAJ: TCR alpha joining region. 2A: the self-cleaving Porcine teschovirus 2A sequence. pA: bovine growth hormone polyA sequence.
Figure 6B:
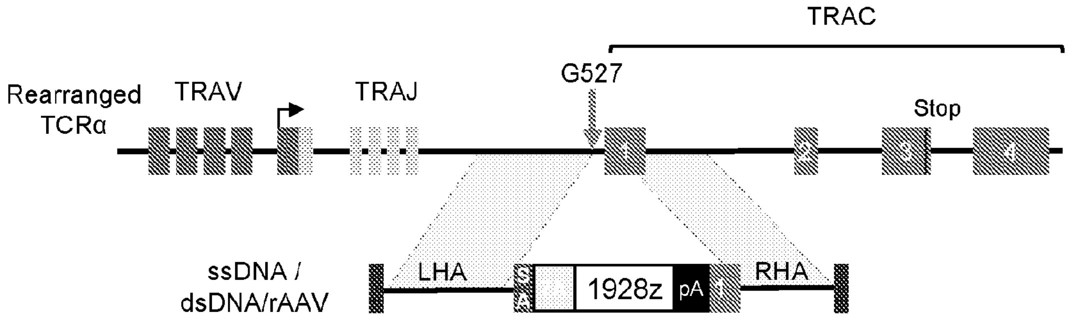
Figure 6C:
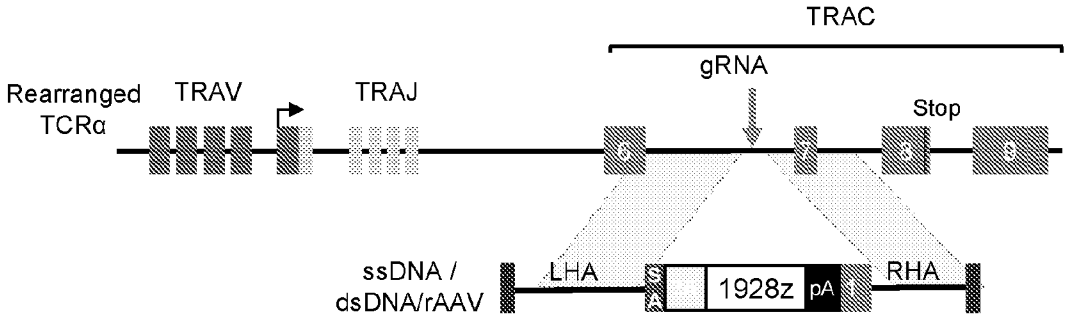
FIGS. 6C and 6D: Schematic representations of CRISPR/Cas9-targeted integration into the TRAC locus using gRNAs targeting different regions in the locus.
Figure 6D:
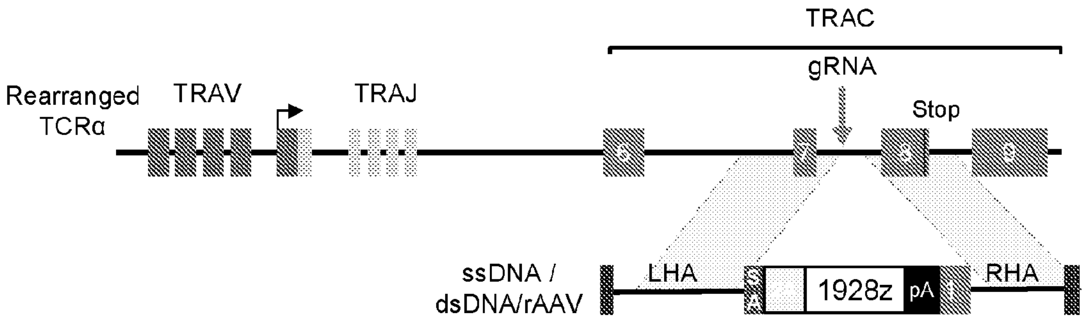
Figure 6E:
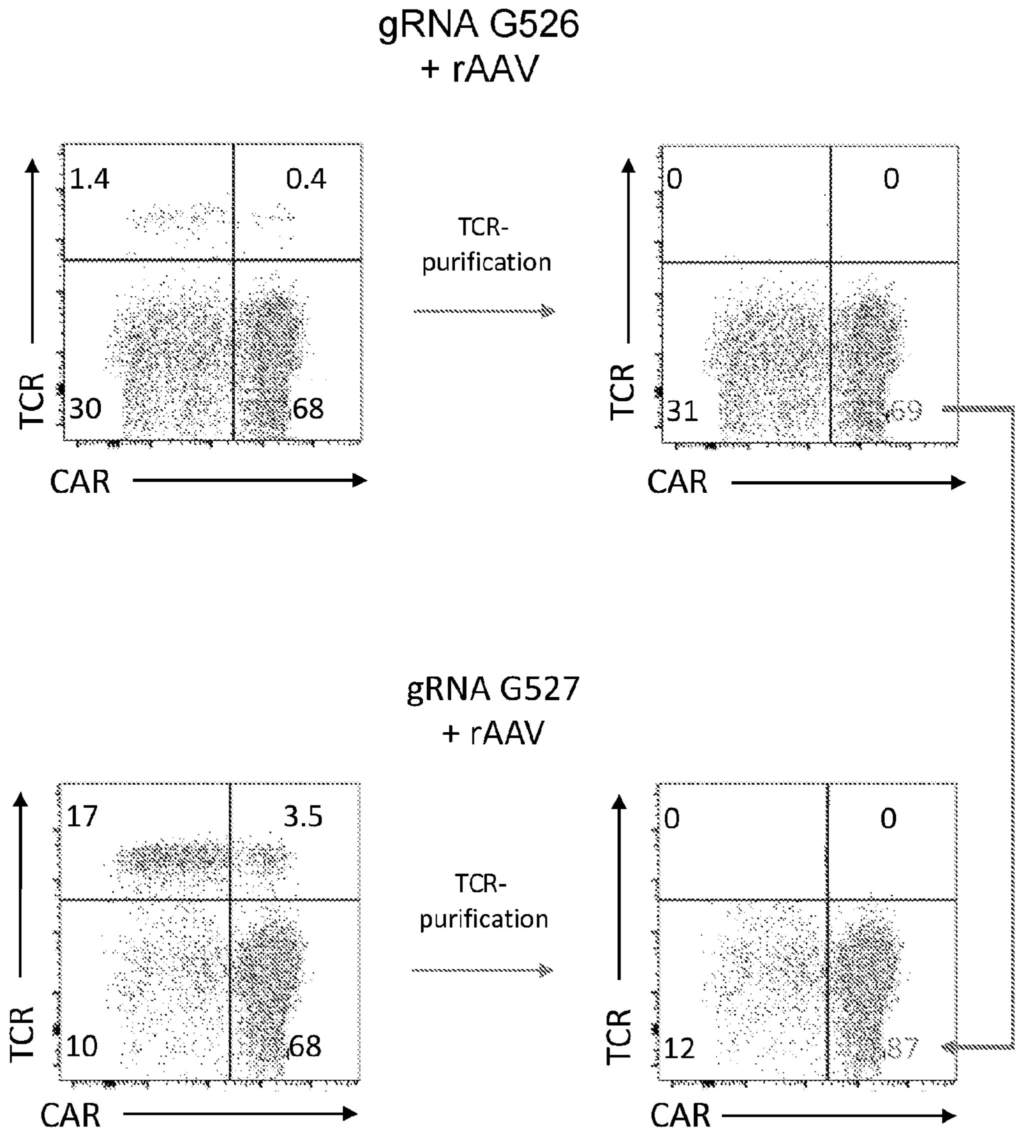
FIG. 6E: Representative TCR/CAR flow plots of T cells electroporation with Cas9 and TRAC gRNAs RNP and transduced with rAAV, before and after TCR negative purification.

In some embodiments, a gRNA can have a sequence having at least 85% (e.g., 85%, 87%, 89%, 91%, 93%, 95%, 97%, 99%, or 100%) identity to a sequence of any one of SEQ ID NOS:2-9 (e.g., gRNA G526, gRNA G527, gRNA G528, gRNA G529, gRNA G530, gRNA G531, gRNA G532, and gRNA G533). As show in FIG. 5, gRNA G526, gRNA G527, gRNA G528, and gRNA G529 each targets a region in the TRAC locus that contains both an intronic region and an exonic region. Further, gRNA G530, gRNA G531, gRNA G532, and gRNA G533 each targets a region in the TRAC locus that is an intronic region.

In some embodiments, a gRNA can have a sequence having at least 85% (e.g., 85%, 87%, 89%, 91%, 93%, 95%, 97%, 99%, or 100%) identity to a sequence of any one of SEQ ID NOS:17-28 (e.g., gRNA G542, gRNA G543, gRNA G544, gRNA G545, gRNA G546, gRNA G547, gRNA G548, gRNA G549, gRNA G550, gRNA G551, gRNA G552, and gRNA G553). gRNA G542, gRNA G543, gRNA G544, gRNA G545, gRNA G546, gRNA G547, gRNA G548, gRNA G549, gRNA G550, gRNA G551, gRNA G552, and gRNA G553 each targets a region in the TRAC locus that contains an intronic region.

In some embodiments, a gRNA can have a sequence having at least 85% (e.g., 85%, 87%, 89%, 91%, 93%, 95%, 97%, 99%, or 100%) identity to a sequence of any one of SEQ ID NOS:29-40 (e.g., gRNA G571, gRNA G572, gRNA G573, gRNA G574, gRNA G575, gRNA G576, gRNA G577, gRNA G578, gRNA G579, gRNA G580, gRNA G581, and gRNA G582). gRNA G571, gRNA G572, gRNA G573, gRNA G574, gRNA G575, gRNA G576, gRNA G577, gRNA G578, gRNA G579, gRNA G580, gRNA G581, and gRNA G582 each targets a region in the B2M locus. In some embodiments, the B2M locus comprises the sequence of GenBank Gene ID:567.

In some embodiments, a gRNA can have a sequence having at least 85% (e.g., 85%, 87%, 89%, 91%, 93%, 95%, 97%, 99%, or 100%) identity to a sequence of any one of SEQ ID NOS:41-52 (e.g., gRNA G559, gRNA G560, gRNA G561, gRNA G562, gRNA G563, gRNA G564, gRNA G565, gRNA G566, gRNA G567, gRNA G568, gRNA G569, and gRNA G570). gRNA G559, gRNA G560, gRNA G561, gRNA G562, gRNA G563, gRNA G564, gRNA G565, gRNA G566, gRNA G567, gRNA G568, gRNA G569, and gRNA G570 each targets a region in the CD4 locus. In some embodiments, the CD4 locus comprises the sequence of GenBank Gene ID:920.

Provided herein are compositions comprising a gRNA, wherein the gRNA comprises the sequence of CTGGATATCTGTGGGACAAG (SEQ ID NO:3; gRNA G527), ATCTGTGGGACAAGAGGATC (SEQ ID NO:4; gRNA G528), TCTGTGGGACAAGAGGATCA (SEQ ID NO:5; gRNA G529), GGGACAAGAGGATCAGGGTT (SEQ ID NO:6; gRNA G530), TCTTTGCCCCAACCCAGGCT (SEQ ID NO:7; gRNA G531), CTTTGCCCCAACCCAGGCTG (SEQ ID NO:8; gRNA G532), or TGGAGTCCAGATGCCAGTGA (SEQ ID NO:9; gRNA G533). The gRNA having the sequence of SEQ ID NO:3 targets nucleotides 798 to 817 of the TRAC locus, the sequence of which is shown in SEQ ID NO: 1. The gRNA having the sequence of SEQ ID NO:4 targets nucleotides 792 to 811 of the TRAC locus. The gRNA having the sequence of SEQ ID NO:5 targets nucleotides 791 to 810 of the TRAC locus. The gRNA having the sequence of SEQ ID NO:6 targets nucleotides 786 to 805 of the TRAC locus. The gRNA having the sequence of SEQ ID NO:7 targets nucleotides 746 to 765 of the TRAC locus. The gRNA having the sequence of SEQ ID NO:8 targets nucleotides 745 to 764 of the TRAC locus. The gRNA having the sequence of SEQ ID NO:9 targets nucleotides 727 to 746 of the TRAC locus. As shown in FIG. 1A, the gRNA having the sequence of SEQ ID NO:3 hybridizes to a portion at the 5' terminus of the TRAC exon 6 and a portion of an intron (e.g., intro 5) located upstream from the TRAC exon 6.

In another aspect, a gRNA having the sequence of TCAGGGTTCTGGATATCTGT (SEQ ID NO:2) can also be used to target the TRAC locus. The gRNA having the sequence of SEQ ID NO:2 targets nucleotides 806 to 825 of the TRAC locus. As shown in FIG. 1A, the gRNA having the sequence of SEQ ID NO:2 also hybridizes to a portion at the 5' terminus of the TRAC exon 6 and a portion of an intron (e.g., intron 5) located upstream from the TRAC exon 6.

FIGS. 6A-6D show schematic representations of CRISPR/Cas9-targeted integration into the TRAC locus using different gRNAs.

Also provided herein are compositions comprising a gRNA, wherein the gRNA comprises the sequence of any one of SEQ ID NOS:17-52.

Further, having a high concentration of the homology-directed-repair template (HDRT) at the site of cleavage can also promote a high level of HDR. In this aspect, the HDRT can be fused to one or more Cas protein target sequences, which can interact with and be bound by the Cas protein via a gRNA to "shuttle" the HDRT to the desired cellular location in proximity to the targeted nucleic acid (e.g., the TRAC locus) to enhance gene modification efficiency. In some embodiments, a Cas protein target sequence is also referred to as shuttle sequence herein.

In some embodiments of an HDRT fused to one or more Cas protein target sequences, the Cas protein target sequence is hybridized to a complementary polynucleotide sequence to form a double-stranded duplex, as shown in FIG. 1B. In some embodiments, the HDRT can be a single-stranded polynucleotide. In other embodiments, the HDRT can be a double-stranded polynucleotide. In some embodiments, the HDRT can be a single-stranded polynucleotide and it is fused to one or more Cas protein target sequences, in which each Cas protein target sequence is hybridized to a complementary polynucleotide sequence. In particular embodiments, an HDRT is fused to two Cas protein target sequences. For example, a first Cas protein target sequence can be fused to the 5' terminus of the HDRT and a second Cas protein target sequence can be fused to the 3' terminus of the HDRT. In certain embodiments, the HDRT has a sequence having at least 85% (e.g., 85%, 87%, 89%, 91%, 93%, 95%, 97%, 99%, or 100%) identity to the sequence of SEQ ID NO:10 or 11, each of which contains the B-cell maturation antigen (BCMA)-CAR sequence. In other embodiments, instead of a CAR or an exogenous protein (e.g., an exogenous intracellular or cell surface protein (e.g., an exogenous TCR)), transgenes for immunotherapy, such as a Syn-Notch gene or a Mini-Notch gene, can be integrated into the genome of a T cell. Other examples of transgenes that can be targeted by compositions described herein include, but are not limited to, chimeric receptor (e.g., chimeric antigen receptor, chimeric co-stimulatory receptor, switch receptor (fusion between the extracellular and intracellular of two receptors, such as but not limited to PD1/28, CD80/4-1BB, TGFBR/4-1BB), T cell receptor and variants thereof (e.g., HLA-independent TCR), SynNotch and variants thereof, receptor modulating allo-immunity (e.g., CD47, HLA-E, and ADR (Alloimmune Defense Receptors)), CD4, CD8, CD95L (FasL), and transcription factors (e.g., TOX, TCF1, IRF8, BTAF, Fli1, and c-Jun).

The compositions described herein can further contain a Cas protein, such as Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, or a variant thereof. In particular embodiments, the Cas protein is Cas9 nuclease. Additional description of Cas proteins is provided further herein.

In some embodiments, instead of a Cas protein, a tailored endonuclease, such as meganuclease, Zinc-Finger Nuclease (ZFN), transcription activator-like (TAL) Effector Nuclease (TALEN), homing endonuclease, or Mega-Tal, can be used to bind to one or more shuttle sequences fused to the HDRT and transport the HDRT to the site of gene modification.

In some embodiments, the Cas protein is fused to a nuclear localization signal (NLS) sequence. Examples of NLS sequences are known in the art, e.g., as described in Lange et al., *J Biol Chem.* 282(8):5101-5, 2007, and also include, but are not limited to, AVKRPAATKKAGQAKKKKLD (SEQ ID NO:12), MSRRRKANPTKLSENAKKLAKEVEN (SEQ ID NO:13), PAAKRVKLD (SEQ ID NO:14), KLKIKRPVK (SEQ ID NO:15), and PKKKRKV (SEQ ID NO:16). Examples of other peptide or proteins that can be fused to a Cas protein, such as cell-penetrating peptides and cell-targeting peptides are available in the art and described, e.g., Vivès et al., *Biochim Biophys Acta.* 1786(2):126-38, 2008. In certain embodiments, the Cas protein has nuclease activity. In yet other embodiments, the Cas protein does not have nuclease activity.

In some embodiments, a composition described herein comprises a gRNA having the sequence of any one of SEQ ID NOS:2-9 and 17-52 and a Cas protein (e.g., Cas9 nuclease). In some embodiments, the gRNA and the Cas protein can be incubated together, e.g., at 37° C. for 30 minutes, to form a ribonucleoprotein (RNP) complex. Further, an anionic polymer can be added to the composition to stabilize the RNP complex and prevent aggregation. Without being bound by any theory, an anionic polymer can may interact favorably with the Cas protein, which is positively-charged at physiological pH, and stabilize the RNP complex into dispersed particles, prevent aggregation, and improve nuclease editing activity and efficiency. Examples of anionic polymers include, but are not limited to, a polyglutamic acid (PGA), a polyaspartic acid, or a polycarboxyglutamic acid. Additional description of anionic polymers is provided in detail further herein.

Figure 8A:
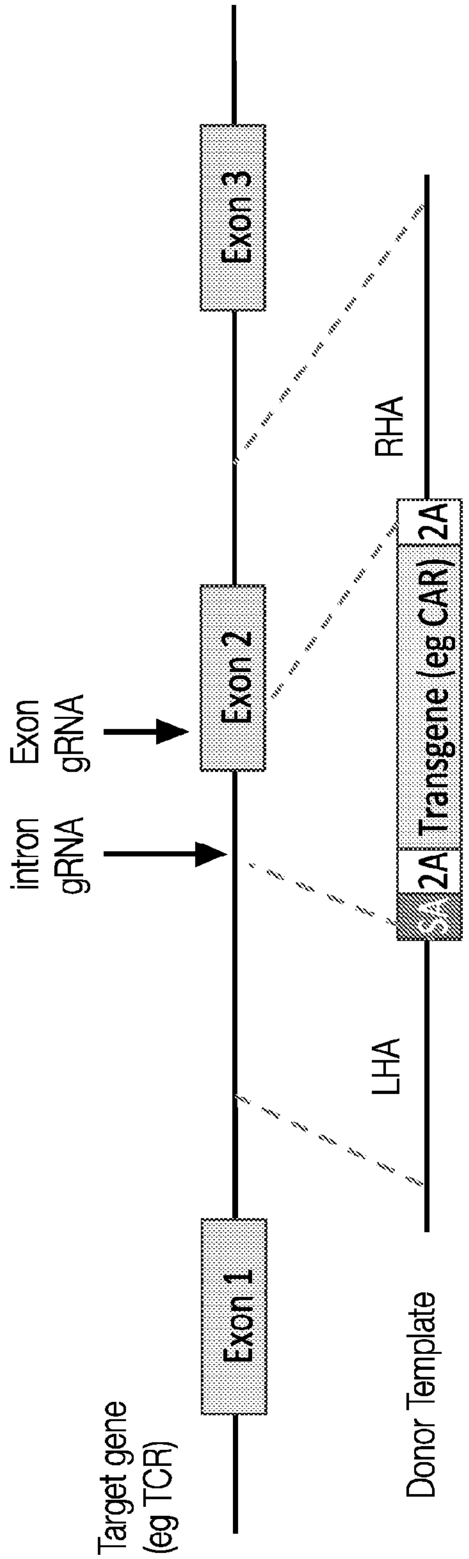
FIG. 8A shows a schematic representation of a KI with an intronic or exonic gRNA at the TRAC locus.
Figure 8B:
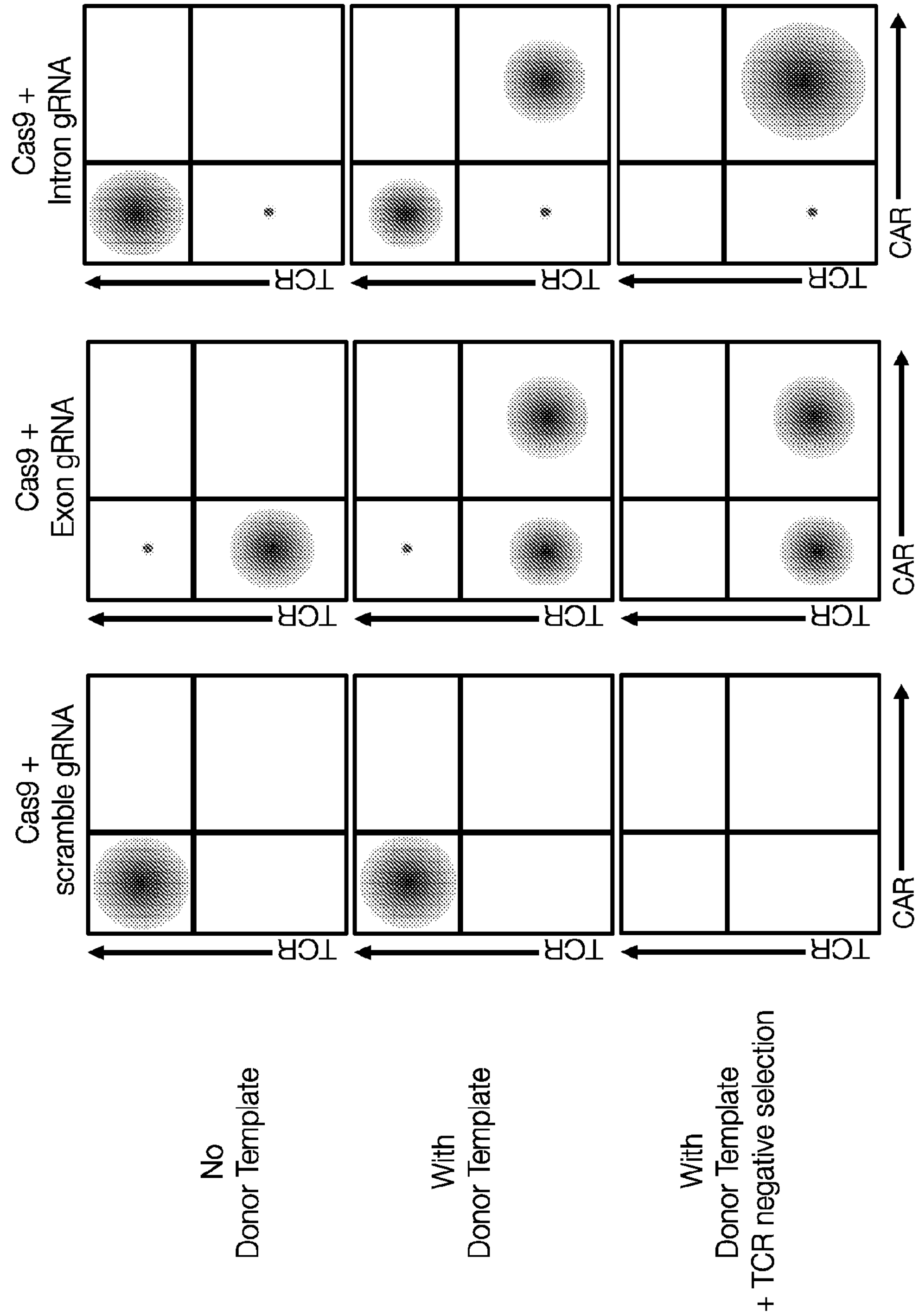
FIG. 8B shows a schematic flow plot of T cells engineered with the indicated gRNA and donor template. The bottom line shows the improved enrichment of CAR positive cells after TCR negative selection.

The compositions described herein can be used for modifying an endogenous cell surface protein (e.g., an endogenous TCR) in a cell (e.g., a T cell) with a CAR or an exogenous protein (e.g., an exogenous intracellular or cell surface protein (e.g., an exogenous TCR)). By modifying a gene in the cell surface protein locus (e.g., TRAC locus), knockin of the CAR or the exogenous protein (e.g., an exogenous intracellular or cell surface protein (e.g., an exogenous TCR)) can simultaneously knockout the endogenous cell surface protein (e.g., endogenous TCR). Further, the method offers the advantage that by selecting for modified cells that are negative for the endogenous cell surface protein, the method is also enriching for cells that have the CAR or exogenous protein knockin. FIG. 8A shows a schematic representation of a KI with an intronic or exonic gRNA at the TRAC locus. Further, a schematic flow plot of T cells engineered with the indicated gRNA and donor template is demonstrated in FIG. 8B. The bottom line in FIG. 8B shows the improved enrichment of CAR positive cells after TCR negative selection. To modified a gene in the cell surface protein locus (e.g., TRAC locus), the gRNA, Cas protein, and HDRT can be introduced into the T cell using different techniques available in the art, such as electroporation and vial delivery, which are described in detail further herein.

Examples of a gene that can be modified by compositions described herein for knockin and negative selection enrichment include, but are not limited to, TRAC, TRBC, TRGC, TRDC, CD3 Delta, CD3 Epsilon, CD3 Gamma, CD3 Zeta (CD247), B2M, CD4, CD8 alpha, CD8 beta, CTLA4, PD-1, TIM-3, LAG3, TIGIT, CD28, CD25, CD69, CD95 (Fas), CD52, CD56, CD38, KLRG-1, and NK specific genes (e.g., NKG2A, NKG2C, NKG2D, NKp46, CD16, CD84, CD84, 2B4, and KIR-L).

In other embodiments, the compositions and methods described herein can be used to modify multiple cell surface proteins at multiple genomic loci (e.g., at least two, three, four, or five genomic loci), i.e., multiple simultaneous intronic knockins. The multiple cell surface proteins can be replaced with different CARS or exogenous proteins (e.g., exogenous intracellular or cell surface proteins). Modified cells that contain all of the desired CARS or exogenous proteins (e.g., exogenous intracellular or cell surface proteins) can be enriched in a negative selection, for example, using antibodies that target the endogenous cell surface proteins. In this manners, cells that contain one or more of the endogenous cell surface proteins that did not get replaced by the desired CARS or exogenous proteins (e.g., exogenous intracellular or cell surface proteins) can all be pulled out using the antibodies, subsequently enriching for cells containing all of the desired CARs or exogenous proteins (e.g., exogenous intracellular or cell surface proteins).

For example, in some embodiments, multiple simultaneous intronic knockins can contain three exogenous proteins (e.g., exogenous intracellular or cell surface proteins) replacing three endogenous cell surface proteins at three different loci. For example, a recombinant MHC-I restricted TCR can replace an endogenous TCR at TRAC locus; an NK cell modulator (e.g., an HLA-E (HLA class I histocompatibility antigen, alpha chain E) protein) can replace an endogenous B2M protein at B2M locus; and a CD8 (e.g., CD8 alpha and beta chains) can replace an endogenous CD4 protein at CD4 locus. To negatively enrich for cells that contain all three of the recombinant MHC-I restricted TCR, HLA-E, and CD8, antibodies that target the endogenous TCR, B2M, and CD4 can be used to pull out cells that still contain one of the endogenous proteins (e.g. endogenous TCR, B2M, and CD4), two of the endogenous proteins, or all three of the endogenous proteins, subsequently enriching for cells containing all three of the recombinant MHC-I restricted TCR, HLA-E, and CD8. The disclosure also provides a method for modifying at least two or more endogenous cell surface proteins in a T cell, comprising introducing into the T cell a first composition comprising a first guide RNA (gRNA) comprising the sequence of any one of SEQ ID NOS:2-9 and 17-52 and a second composition comprising a second gRNA comprising the sequence of any one of SEQ ID NOS:2-9 and 17-52, wherein the two or more endogenous cell surface proteins are different and wherein the first gRNA and the second gRNA are different.

IV. Methods of Delivery

The compositions described herein for use in methods of modifying an endogenous cell surface protein (e.g., endogenous TCR) in a cell (e.g., a T cell) can be delivered into the T cell using a number of techniques in the art. In some embodiments, the composition can be introduced into the cell via electroporation. In some embodiments, a ribonucleoprotein (RNP) complex containing a Cas protein (e.g., Cas9 nuclease) and a gRNA can be formed first, then electroporated into the cell. Methods, compositions, and devices for electroporation are available in the art, e.g., those described in WO2006/001614 or Kim, J. A. et al. *Biosens. Bioelectron.* 23, 1353-1360 (2008). Additional or alternative methods, compositions, and devices for electroporation can include those described in U.S. Patent Appl. Pub. Nos. 2006/0094095; 2005/0064596; or 2006/0087522. Additional or alternative methods, compositions, and devices for electroporation can include those described in Li, L. H. et al. *Cancer Res. Treat.* 1, 341-350 (2002); U.S. Pat. Nos. 6,773,669; 7,186,559; 7,771,984; 7,991,559; 6,485,961; and 7,029,916; and U.S. Patent Appl. Pub. Nos: 2014/0017213; and 2012/0088842. Additional or alternative methods, compositions, and devices for electroporation can include those described in Geng, T. et al. *J. Control Release* 144, 91-100 (2010); and Wang, J., et al. *Lab Chip* 10, 2057-2061 (2010).

In other embodiments, the Cas protein, the HDRT, and the gRNA in a composition described herein can be introduced into the cell via viral delivery using a viral vector. For example, viral vectors can be based on vaccinia virus, poliovirus, adenovirus, adeno-associated virus (AAV) (e.g., recombinant AAV (rAAV)), SV40, herpes simplex virus, human immunodeficiency virus, and the like. A retroviral vector can be based on Murine Leukemia Virus, spleen necrosis virus, and vectors derived from retroviruses such as Rous Sarcoma Virus, Harvey Sarcoma Virus, avian leukosis virus, a lentivirus (e.g., integration deficient lentivirus), human immunodeficiency virus, myeloproliferative sarcoma virus, mammary tumor virus, and the like. In some embodiments, a retroviral vector can be an integration deficient gamma retroviral vector. Other useful expression vectors are known to those of skill in the art, and many are commercially available. The following exemplary vectors are provided by way of example for eukaryotic host cells: pXT1, pSG5, pSVK3, pBPV, pMSG, and pSVLSV40. Examples of techniques that may be used to introduce a viral vector into a cell include, but not limited to, viral or bacteriophage infection, transfection, protoplast fusion, lipofection, calcium phosphate precipitation, polyethyleneimine (PEI)-mediated transfection, DEAE-dextran mediated transfection, liposome-mediated transfection, calcium phosphate precipitation, nanoparticle-mediated nucleic acid delivery, and the like.

V. Methods of Selection

Cells that have the endogenous cell surface protein (e.g., endogenous TCR) is replaced with a CAR or an exogenous protein (e.g., an exogenous intracellular or cell surface protein (e.g., an exogenous TCR)) can be selected using various techniques available in the art. By selecting for modified cells that do not express the endogenous cell surface protein (e.g., endogenous TCR), the method is also enriching for cells that have the CAR or exogenous protein (e.g., an exogenous intracellular or cell surface protein (e.g., an exogenous TCR)) knockin. In some embodiments, the selection method targets and selectively pulls out the unmodified T cells that still express the endogenous cell surface protein, leaving the modified T cells that express the CAR or the exogenous protein (e.g., exogenous intracellular or cell surface protein) in the supernatant, which is also referred to as negative selection. In a negative selection, the selection method targets the undesired component (e.g., the endogenous cell surface protein that is supposed to be modified), and leaves the desired population of modified T cells untouched. In some embodiments, negative selection is more efficient (less cell loss), less cytotoxic on the cells, and faster than positive selection. In a positive selection, the selection method targets the desired component or a component that is introduced into the modified T cells (e.g., the CAR, the exogenous protein (e.g., exogenous intracellular or cell surface protein), or a protein that is co-expressed with the CAR or the exogenous protein (e.g., exogenous intracellular or cell surface protein)). Moreover, positive selection targeting the CAR or the exogenous protein can lead to T cell activation, which is detrimental for antitumor activity of the T cells. Further, positive selection targeting a protein that could be co-expressed with a CAR, e.g., a truncated EGFR, requires increasing the size of the HDRT, which can have a negative impact knockin efficiency and cell viability.

In a particular aspect, a population of T cells is provided. The population of T cells can comprise the modified cells described herein. The modified cell can be within a heterogeneous population of cells. The population of cells can be heterogeneous with respect to the percentage of cells that are genomically edited. A population of T cells can have greater than 10%, greater than 20%, greater than 30%, greater than 40%, greater than 50%, greater than 60%, greater than 70%, greater than 80%, or greater than 90% of the population comprise an integrated nucleotide sequence that encodes the CAR or the exogenous protein (e.g., an exogenous cell surface protein (e.g., an exogenous TCR)).

Methods for selecting for modified T cells that have an endogenous cell surface protein (e.g., endogenous TCR) in the T cells replaced with a CAR or an exogenous protein (e.g., an exogenous intracellular or cell surface protein (e.g., an exogenous TCR)) from the population of T cells are provided. After a composition described herein that contains a Cas protein, a gRNA targeting the cell surface protein locus (e.g., TRAC locus), and an HDRT that encodes the CAR or the exogenous protein (e.g., an exogenous intracellular or cell surface protein (e.g., an exogenous TCR)) is introduced (e.g., introduced via electroporation or viral delivery) into a population of T cells and the cells are incubated for a few days for the modification to take place, the modified T cells can be selected (e.g., negatively selected) by contacting the population of T cells with antibody-coated magnetic beads, in which the antibodies on the magnetic beads target the endogenous cell surface protein (e.g., endogenous TCR). In this manner, the T cells that are not modified and still express the endogenous cell surface protein (e.g., endogenous TCR) can be separated from the modified T cells that have the endogenous cell surface protein replaced by the CAR or the exogenous protein (e.g., exogenous intracellular or cell surface protein). In cases where the endogenous cell surface protein is replaced with an exogenous protein (e.g., exogenous intracellular or cell surface protein (e.g., an exogenous recombinant TCR)), one has to ensure that the epitope recognized by the antibody is only present in the endogenous cell surface protein (e.g., endogenous TCR) and not present in the exogenous protein (e.g., an exogenous intracellular or cell surface protein (e.g., an exogenous recombinant TCR)). The antibody-coated magnetic beads bound to the unmodified T cells can then be separated from the modified T cells using a magnetic separation rack. The supernatant, which contains the modified T cells, can be collected into a separate container.

In some cases, a population of T cells are removed from a subject, modified using any of the compositions and methods described herein, and administered to the subject. In other cases, a composition described herein can be delivered to the subject in vivo. See, for example, U.S. Pat. No. 9,737,604 and Zhang et al. "Lipid nanoparticle-mediated efficient delivery of CRISPR/Cas9 for tumor therapy," *NPG Asia Materials* Volume 9, page e441 (2017).

The compositions described herein can be used in methods of modifying an endogenous cell surface protein (e.g., endogenous TCR) in a cell (e.g., a T cell) with a CAR or an exogenous protein (e.g., an exogenous intracellular or cell surface protein (e.g., an exogenous TCR)). The cell can be in vitro, ex vivo, or in vivo. In some embodiments, the T cell is a regulatory T cell, an effector T cell, or a naïve T cell. In some embodiments, the T cell is a $CD4^+$ T cell. In some embodiments, the T cell is a $CD8^+$ T cell. In some embodiments, the T cell is a $CD4^+CD8^+$ T cell. In some embodiments, the T cell is a $CD4^-CD8^-$ T cell. In some embodiments, the T cell is an $\alpha\beta$ cell. In some embodiments, the T cell is a $\gamma\delta$ T cell. In some embodiments, the methods further comprise expanding the population of modified T cells.

In addition, the compositions and methods described herein can also be applied to other cell types, such as, but are not limited to, hematopoietic stems, progenitor cells, T cells (CD4 T cells, CD8 T cells, T-regulatory cells, gamma/delta T cells), natural killer (NK) cells, NK T cells, iPS/ES cells, iPS/ES-derived NK cells, iPS/ES-derived NK T cells, B cells, myeloid cells, iPS/ES derived B cells, and iPS/ES derived myelod cells.

VI. Guide RNAs

A Cas protein can be guided to its target nucleic acid by a guide RNA (gRNA). A gRNA is a version of the naturally occurring two-piece guide RNA (crRNA and tracrRNA) engineered into a two-piece gRNA or a single, continuous sequence. A gRNA can contain a guide sequence (e.g., the crRNA equivalent portion of the gRNA) that targets the Cas protein to the target nucleic acid and a scaffold sequence that interacts with the Cas protein (e.g., the tracrRNAs equivalent portion of the gRNA). A gRNA can be selected using a software. As a non-limiting example, considerations for selecting a gRNA can include, e.g., the PAM sequence for the Cas protein to be used, and strategies for minimizing off-target modifications. Tools, such as NUPACK® and the CRISPR Design Tool, can provide sequences for preparing the gRNA, for assessing target modification efficiency, and/or assessing cleavage at off-target sites. As described herein, the location in the endogenous cell surface protein genomic locus (e.g., TRAC genomic locus) that the gRNA targets is important in promoting a high level of HDR and low level of NHEJ. Moreover, without being bound by any theory, having a gRNA targeting an intronic region, or a portion thereof, in the cell surface protein locus (e.g., TRAC locus) can lead to high level of HDR and low level of NHEJ. In particular embodiments, a gRNA targeting a region in the cell surface protein locus (e.g., TRAC locus) can have a sequence of any one of SEQ ID NOS:2-9 and 17-52. In some embodiments, a gRNA targeting a region in the TRAC locus can have a sequence of any one of SEQ ID NOS:2-9.

Guide Sequence

The guide sequence in the gRNA may be complementary to a specific sequence within a target nucleic acid. The 3' end of the target nucleic acid sequence can be followed by a PAM sequence. Approximately 20 nucleotides upstream of the PAM sequence is the target nucleic acid. In general, a Cas9 protein or a variant thereof cleaves about three nucleotides upstream of the PAM sequence. The guide sequence in the gRNA can be complementary to either strand of the target nucleic acid.

In some embodiments, the guide sequence of a gRNA may comprise about 10 to about 2000 nucleic acids, for example, about 10 to about 100 nucleic acids, about 10 to about 500 nucleic acids, about 10 to about 1000 nucleic acids, about 10 to about 1500 nucleic acids, about 10 to about 2000 nucleic acids, about 50 to about 100 nucleic acids, about 50 to about 500 nucleic acids, about 50 to about 1000 nucleic acids, about 50 to about 1500 nucleic acids, about 50 to about 2000 nucleic acids, about 100 to about 500 nucleic acids, about 100 to about 1000 nucleic acids, about 100 to about 1500 nucleic acids, about 100 to about 2000 nucleic acids, about 500 to about 1000 nucleic acids, about 500 to about 1500 nucleic acids, about 500 to about 2000 nucleic acids, about 1000 to about 1500 nucleic acids, or about 1000 to about 2000 nucleic acids. In some embodiments, the guide sequence of a gRNA comprises about 100 nucleic acids at the 5' end of the gRNA that can direct the Cas protein to the target nucleic acid site using RNA-DNA complementarity base pairing. In some embodiments, the guide sequence comprises 20 nucleic acids at the 5' end of the gRNA that can direct the Cas protein to the target nucleic acid site using RNA-DNA complementarity base pairing. In other embodiments, the guide sequence comprises less than 20, e.g., 19, 18, 17, 16, 15 or less, nucleic acids that are complementary to the target nucleic acid site. In some instances, the guide sequence in the gRNA contains at least one nucleic acid mismatch in the complementarity region of the target nucleic acid site. In some instances, the guide sequence contains about 1 to about 10 nucleic acid mismatches in the complementarity region of the target nucleic acid site.

Scaffold Sequence

The scaffold sequence in the gRNA can serve as a protein-binding sequence that interacts with the Cas protein or a variant thereof. In some embodiments, the scaffold sequence in the gRNA can comprise two complementary stretches of nucleotides that hybridize to one another to form a double-stranded RNA duplex (dsRNA duplex). The scaffold sequence may have structures such as lower stem, bulge, upper stem, nexus, and/or hairpin. In some embodiments, the scaffold sequence in the gRNA can be between about 90 nucleic acids to about 120 nucleic acids, e.g., about 90 nucleic acids to about 115 nucleic acids, about 90 nucleic acids to about 110 nucleic acids, about 90 nucleic acids to about 105 nucleic acids, about 90 nucleic acids to about 100 nucleic acids, about 90 nucleic acids to about 95 nucleic acids, about 95 nucleic acids to about 120 nucleic acids, about 100 nucleic acids to about 120 nucleic acids, about 105 nucleic acids to about 120 nucleic acids, about 110 nucleic acids to about 120 nucleic acids, or about 115 nucleic acids to about 120 nucleic acids.

VII. Cas Protein

In some embodiments, the Cas protein has nuclease activity. For example, the Cas protein can modify the target nucleic acid by cleaving the target nucleic acid. The cleaved target nucleic acid can then undergo homologous recombination with a nearby HDRT. For example, the Cas protein can direct cleavage of one or both strands at a location in a target nucleic acid. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, variants thereof, mutants thereof, and derivatives thereof. There are three main types of Cas proteins (type I, type II, and type III), and 10 subtypes including 5 type I, 3 type II, and 2 type III proteins (see, e.g., Hochstrasser and Doudna, *Trends Biochem Sci,* 2015:40(1): 58-66). Type II Cas proteins include Cas1, Cas2, Csn2, Cas9, and Cfp1. These Cas proteins are known to those skilled in the art. For example, the amino acid sequence of the *Streptococcus pyogenes* wild-type Cas9 polypeptide is set forth, e.g., in NBCI Ref. Seq. No. NP_269215, and the amino acid sequence of *Streptococcus thermophilus* wild-type Cas9 polypeptide is set forth, e.g., in NBCI Ref. Seq. No. WP_011681470.

Cas proteins, e.g., Cas9 nucleases, can be derived from a variety of bacterial species including, but not limited to, *Veillonella atypical, Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes*, and *Francisella novicida.*

Cas9 protein refers to an RNA-guided double-stranded DNA-binding nuclease protein or nickase protein. Wild-type Cas9 nuclease has two functional domains, e.g., RuvC and HNH, that cut different DNA strands. Cas9 can induce double-strand breaks in genomic DNA (target nucleic acid) when both functional domains are active. The Cas9 enzyme can comprise one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor*, and *Campylobacter*. In some embodiments, the Cas9 can be a fusion protein, e.g., the two catalytic domains are derived from different bacteria species.

In some embodiments, a Cas protein can be a Cas protein variant. For example, useful variants of the Cas9 nuclease can include a single inactive catalytic domain, such as a $RuvC^{-}$ or $HNH^{-}$ enzyme or a nickase. A Cas9 nickase has only one active functional domain and can cut only one strand of the target nucleic acid, thereby creating a single strand break or nick. In some embodiments, the Cas9 nuclease can be a mutant Cas9 nuclease having one or more amino acid mutations. For example, the mutant Cas9 having at least a D 10A mutation is a Cas9 nickase. In other embodiments, the mutant Cas9 nuclease having at least a H840A mutation is a Cas9 nickase. Other examples of mutations present in a Cas9 nickase include, without limitation, N854A and N863A. A double-strand break can be introduced using a Cas9 nickase if at least two DNA-targeting RNAs that target opposite DNA strands are used. A double-nicked induced double-strand break can be repaired by NHEJ or HDR (Ran et al., 2013, Cell, 154:1380-1389). Non-limiting examples of Cas9 nucleases or nickases are described in, for example, U.S. Pat. Nos. 8,895,308; 8,889,418; and 8,865,406 and U.S. Application Publication Nos. 2014/0356959, 2014/0273226 and 2014/0186919. The Cas9 nuclease or nickase can be codon-optimized for the target cell or target organism.

In some embodiments, a Cas protein variant that lacks cleavage (e.g., nickase) activity. A Cas protein variant may contain one or more point mutations that eliminates the protein's nickase activity. In some embodiments, Cas protein variants that lack cleavage activity can bind to a Cas protein target sequence fused to an HDRT via a gRNA that hybridizes to the Cas protein target sequence. In other embodiments, Cas protein variants that lack cleavage activity can be fused to other proteins and serve as targeting domains to direct the other proteins to the target nucleic acid. For example, Cas protein variants without nickase activity may be fused to transcriptional activation or repression domains to control gene expression (Ma et al., *Protein and Cell,* 2(11):879-888, 2011; Maeder et al., *Nature Methods,* 10:977-979, 2013; and Konermann et al., *Nature,* 517:583-588, 2014).

In some embodiments, the Cas protein can be a high-fidelity or enhanced specificity Cas9 polypeptide variant with reduced off-target effects and robust on-target cleavage. Non-limiting examples of Cas9 polypeptide variants with improved on-target specificity include the SpCas9 (K855A), SpCas9 (K810A/K1003A/R1060A) (also referred to as eSpCas9(1.0)), and SpCas9 (K848A/K1003A/R1060A) (also referred to as eSpCas9(1.1)) variants described in Slaymaker et al., *Science,* 351(6268):84-8 (2016), and the SpCas9 variants described in Kleinstiver et al., *Nature,* 529(7587): 490-5 (2016) containing one, two, three, or four of the following mutations: N497A, R661A, Q695A, and Q926A (e.g., SpCas9-HF1 contains all four mutations).

In some embodiments, a Cas protein variant without any cleavage activity can be a Cas9 polypeptide that contains two silencing mutations of the RuvC1 and HNH nuclease domains (D10A and H840A), which is referred to as dCas9 (Jinek et al., *Science,* 2012, 337:816-821; Qi et al., *Cell,* 152(5):1173-1183). In one embodiment, the dCas9 polypeptide from *Streptococcus pyogenes* comprises at least one mutation at position D10, G12, G17, E762, H840, N854, N863, H982, H983, A984, D986, A987 or any combination thereof. Descriptions of such dCas9 polypeptides and variants thereof are provided in, for example, International Patent Publication No. WO 2013/176772. The dCas9 enzyme can contain a mutation at D10, E762, H983, or D986, as well as a mutation at H840 or N863. In some instances, the dCas9 enzyme can contain a D10A or D10N mutation. Also, the dCas9 enzyme can contain a H840A, H840Y, or H840N. In some embodiments, the dCas9 enzyme can contain D10A and H840A; D10A and H840Y; D10A and H840N; D10N and H840A; D10N and H840Y; or D10N and H840N substitutions. The substitutions can be conservative or non-conservative substitutions to render the Cas9 polypeptide catalytically inactive and able to bind to target nucleic acid.

VIII. Anionic Polymers

In some embodiments of the compositions described herein, an anionic polymer can be added to a composition, e.g., to improve the stability and editing efficiency of Cas protein and gRNA ribonucleoprotein complex (RNP). In some embodiments, the addition of anionic polymers to a composition containing a Cas protein (e.g., a Cas9 protein) or a composition containing a Cas protein (e.g., a Cas9 protein) and gRNA RNP complex can stabilize the Cas protein or the RNP complex and prevent aggregation, leading to high nuclease activity and editing efficiency. Without being bound by any theory, the anionic polymer (e.g., PGA) may interact favorably with the Cas protein, i.e., the anionic polymer (e.g., PGA) may interact favorably with the positively-charged (at physiological pH) Cas9 protein, stabilize the RNP complex into dispersed particles, prevent aggregation, and improve nuclease editing activity and efficiency. An anionic polymer can be water soluble. An anionic polymer can be biologically inert. In some aspects an anionic polymer is not a DNA sequence. An anionic polymer can be capable of undergoing freeze/thaw cycling while retaining full or substantial functionality. An anionic polymer can be lyophilized while retaining full or substantial functionality. An anionic polymer can have a molecular weight of 15,000 to 50,000 kDa (e.g., 15,000 to 45,000 kDa, 15,000 to 40,000 kDa, 15,000 to 35,000 kDa, 15,000 to 30,000 kDa, 15,000 to 25,000 kDa, 15,000 to 20,000 kDa, 20,000 to 50,000 kDa, 25,000 to 50,000 kDa, 30,000 to 50,000 kDa, 35,000 to 50,000 kDa, 40,000 to 50,000 kDa, or 45,000 to 50,000 kDa). An anionic polymer can be polyglutamic acid (PGA). In some embodiments, a single-stranded donor oligonucleotides (ssODN) can be used instead of or in addition to an anionic polymer. Examples of ssODNs are described in, e.g., Okamoto et al., *Scientific Report* 9:4811, 2019; and Hu et al., *Nucleic Acids,* 17:P198, 2019.

An anionic polymer described herein can be added to a composition to stabilize the composition, improve editing, reduce toxicity, and enable lyophilization of the composition without loss of activity. In some embodiments, a composition containing the Cas protein and the anionic polymer is an aqueous composition that appears homogenous, has a clear visual appearance, and is free of cloudy precipitates or aggregates. In some embodiments, a composition containing the Cas protein and gRNA RNP complex and the anionic polymer is an aqueous composition that appears homogenous, has a clear visual appearance, and is free of cloudy precipitates or aggregates. Having a stable composition allows efficiency gene knock-outs and large transgene knock-ins with high cell survival rate. Further, the composition can also be lyophilized for long-term storage and reconstituted for later use. A composition comprising an anionic polymer can also be used in methods of modifying a target nucleic acid, where the target nucleic acid can be removed, replaced by an exogenous nucleic acid sequence, or an exogenous nucleic acid sequence can be inserted within the target nucleic acid.

An anionic polymer that can be added to a composition described herein is a molecule composed of subunits or monomers that has an overall negative charge. An anionic polymer can be an anionic polypeptide or an anionic polysaccharide. An anionic polypeptide is an anionic polymer that has at least 50% (e.g., 55%, 60%, 65%, 70%, 75%, 80%, 85%, 90%, 95%, or 100%) of its subunits or monomers being amino acids, such as acidic amino acids (e.g., glutamic acids and aspartic acids), or derivatives thereof. Examples of anionic polypeptides include, but are not limited to, polyglutamic acid (PGA) (e.g., poly-gamma-glutamic acid), polyaspartic acid, and polycarboxyglutamic acid. In some embodiments, an anionic polypeptide is a PGA (e.g., poly-gamma-glutamic acid), such as a poly(L-glutamic) acid or a poly(D-glutamic) acid. An anionic polypeptide can contain a mixture of glutamic acids and aspartic acids. In some embodiments, at least 50% (e.g., 55%, 60%, 65%, 70%, 75%, 80%, 85%, 90%, 95%, or 100%) of the subunits or monomers in an anionic polypeptide can be glutamic acids and/or aspartic acids. An anionic polysaccharide is an anionic polymer that has at least 50% (e.g., 55%, 60%, 65%, 70%, 75%, 80%, 85%, 90%, 95%, or 100%) of its subunits or monomers being sugar molecules, such as monosaccharides (e.g., fructose, galactose, and glucose) and disaccharides (e.g., hyaluronic acid, lactose, maltose, and sucrose), or derivatives thereof. Examples of anionic polysaccharides include, but are not limited to, hyaluronic acid (HA), heparin, heparin sulfate, and glycosaminoglycan. In some embodiments, at least 50% (e.g., 55%, 60%, 65%, 70%, 75%, 80%, 85%, 90%, 95%, or 100%) of the subunits or monomers in an anionic polysaccharide can be HA. Other examples of anionic polymers include, but are not limited to, poly(acrylic acid) (PAA), poly(methacrylic acid) (PMAA), poly(styrene sulfonate), and polyphosphate.

An anionic polymer herein does not refer to a nucleic acid, such as a deoxyribonucleic acid (DNA), ribonucleic acid (RNA), that is composed entirely of nucleotides. In some embodiments, an anionic polymer can include one or more nucleobases (e.g., guanosine, cytidine, adenosine, thymidine, and uridine) together with other subunits or monomers, such as amino acids and/or small organic molecules (e.g., an organic acid). In some embodiments, at least 50% (e.g., 55%, 60%, 65%, 70%, 75%, 80%, 85%, 90%, 95%, or 100%) of the subunits or monomers in the anionic polymer are not nucleotides or do not contain nucleobases. An anionic polymer can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers). In some embodiments, the anionic polymer has a molecular weight of at least 3 kDa (e.g., 5, 10, 15, 20, 25, 30, 35, 40, 45, or 50 kDa). In some embodiments, the anionic polymer has a molecular weight of between 3 kDa and 50 kDa (e.g., between 3 kDa and 45 kDa, between 3 kDa and 40 kDa, between 3 kDa and 35 kDa, between 3 kDa and 30 kDa, between 3 kDa and 25 kDa, between 3 kDa and 20 kDa, between 3 kDa and 15 kDa, between 3 kDa and 10 kDa, between 3 kDa and 5 kDa, between 5 kDa and 50 kDa, between 10 kDa and 50 kDa, between 15 kDa and 50 kDa, between 20 kDa and 50 kDa, between 25 kDa and 50 kDa, between 30 kDa and 50 kDa, between 35 kDa and 50 kDa, between 40 kDa and 50 kDa, or between 45 kDa and 50 kDa). In some embodiments, the anionic polymer has a molecular weight of between 50 kDa and 150 kDa (e.g., between 50 kDa and 140 kDa, between 50 kDa and 130 kDa, between 50 kDa and 120 kDa, between 50 kDa and 110 kDa, between 50 kDa and 100 kDa, between 50 kDa and 90 kDa, between 50 kDa and 80 kDa, between 50 kDa and 70 kDa, between 50 kDa and 60 kDa, between 60 kDa and 150 kDa, between 70 kDa and 150 kDa, between 80 kDa and 150 kDa, between 90 kDa and 150 kDa, between 100 kDa and 150 kDa, between 110 kDa and 150 kDa, between 120 kDa and 150 kDa, between 130 kDa and 150 kDa, or between 140 kDa and 150 kDa). In some embodiments, the anionic polymer has a molecular weight of between 15 kDa and 50 kDa (e.g., between 15 kDa and 45 kDa, between 15 kDa and 40 kDa, between 15 kDa and 35 kDa, between 15 kDa and 30 kDa, between 15 kDa and 25 kDa, between 15 kDa and 20 kDa, between 20 kDa and 50 kDa, between 25 kDa and 50 kDa, between 30 kDa and 50 kDa, between 35 kDa and 50 kDa, between 40 kDa and 50 kDa, or between 45 kDa and 50 kDa). In some embodiments, a composition described herein has a molar ratio of anionic polymer:Cas protein at between 10:1 and 120:1, e.g., 10:1, 20:1, 30:1, 40:1, 50:1, 60:1, 70:1, 80:1, 90:1, 100:1, 110:1, or, 120:1; between 10:1 and 110:1, between 10:1 and 100:1, between 10:1 and 90:1, between 10:1 and 80:1, between 10:1 and 70:1, between 10:1 and 60:1, between 10:1 and 50:1, between 10:1 and 40:1, between 10:1 and 30:1, between 10:1 and 20:1, between 20:1 and 120:1, between 30:1 and 120:1, between 40:1 and 120:1, between 50:1 and 120:1, between 60:1 and 120:1, between 70:1 and 120:1, between 80:1 and 120:1, between 90:1 and 120:1, between 100:1 and 120:1, or between 110:1 and 120:1.

EXAMPLES

The following examples are provided by way of illustration only and not by way of limitation. Those of skill in the art will readily recognize a variety of non-critical parameters that could be changed or modified to yield essentially the same or similar results.

Example 1—Methods

Cell Culture

Primary adult cells were obtained from healthy human donors from leukoreduction chamber residuals after Trima Accel apheresis. Peripheral blood mononuclear cells were isolated by Ficoll-Paque (GE Healthcare) centrifugation using SepMate tubes (STEMCELL, as per the manufacturer's instructions). Lymphocytes were then further isolated by magnetic negative selection using an EasySep bulk ($CD3^+$) T Cell Isolation kit (STEMCELL, as per the manufacturer's instructions).

Isolated T cells were activated and cultured for 2 d at 0.75 million cells $ml^{-1}$ in XVivo15 medium (Lonza) with 5% fetal bovine serum, 50 μM 2-mercaptoethanol, 10 mM N-acetyl L-cysteine, anti-human CD3/CD28 magnetic Dynabeads (Thermo Fisher) at a bead to cell ratio of 1:1, and a cytokine cocktail of IL-2 at 500 U $ml^{-1}$ (UCSF Pharmacy), IL-7 at 5 ng $ml^{-1}$ (R&D Systems), and IL-15 at 5 ng $ml^{-1}$ (R&D Systems). Activated T cells were collected from their culture vessels, and Dynabeads were removed by placing cells on an EasySep cell separation magnet (STEMCELL) for 5 min.

RNP Formulation

Cas9 RNPs were formulated immediately prior to electroporation. Synthetic CRISPR RNA (crRNA) and trans-activating crRNA (tracrRNA) were chemically synthesized (Dharmacon), resuspended in IDT duplex buffer at a concentration of 160 μM, and stored in aliquots at −80° C. To make gRNA, aliquots of crRNA and tracrRNA were thawed, mixed 1:1 v/v, and annealed by incubation at 37° C. for 30 min to form an 80 μM gRNA solution. Cas9-NLS was purchased from the University of California Berkeley QB3 MacroLab. To make RNPs, gRNA mixed 1:1 v/v with 40 μM Cas9-NLS protein to achieve a 2:1 molar ratio of gRNA: Cas9.5-50 kDa PGA (Sigma) was resuspended to 100 mg $ml^{-1}$ in water, sterile filtered, and mixed with freshly prepared gRNA at a 0.8:1 volume ratio prior to complexing with Cas9 protein for a final volume ratio of gRNA:PGA: Cas9 of 1:0.8:1.

HDR Template Generation

Long double-strand HDR templates encoding left and right homology arms flanking the P2A-BCMA-CAR-P2A insert were cloned into a pUC19 plasmid, which then served as a template for generating a PCR amplicon. PCR primers targeting the left and right homology arms +/− additional gRNA-specific shuttle were used to amplify the HDRT with KAPA HiFi polymerase (Kapa Biosystems). For generation of ssDNA, 5'biotinylation was included on the reverse primer. PCR products were purified by SPRI bead cleanup, and resuspended in water to 0.5-2 μg $\mu l^{-1}$ measured by light absorbance on a NanoDrop spectrophotometer (Thermo Fisher). ssDNA was generated by incubation of biotinylated PCR product with streptavidin-coupled magnetic beads and denaturing in 125 mM NaOH. Supernatant containing the free non-biotinylated strand was neutralized in 60 mM Sodium Acetate, pH 5.2 in 1×TE. ssDNA was concentrated by SPRI bead purification and resuspended in in water to 0.5-2 μg $\mu l^{-1}$. ssDNA shuttle constructs were generated by incubation of long ssDNA backbone with the corresponding 5' and 3' complementary oligonucleotides at molar ratio of 1:1:1.

Electroporation and Analysis

The HDR templates at the described molar amounts were mixed and incubated with 50 pmol RNP/electroporation for at least 15 min prior to mixing with and electroporating into cells. Immediately prior to electroporation in a 96-well format 4D-Nucleofector (Lonza), cells were centrifuged for 10 min at 90 g, medium was aspirated, and cells were resuspended in the electroporation buffer P3 (Lonza) using 20 μl buffer per $0.75\times10^{6}$ cells. Cells were electroporated with pulse code EH-115. Immediately after electroporation, cells were rescued with the addition of 80 μL of growth medium directly into the electroporation well, incubated for 10-20 min, then removed and diluted to $0.5\text{-}1.0\times10^{6}$ cells $ml^{-1}$ in growth medium. Additional fresh growth medium and cytokines were added every 48 h.

At 5 d after electroporation cells were collected for staining and flow cytometry analysis on an Attune N×T flow cytometer with an automated 96-well sampler (Thermo Fisher) sampling a defined volume (60 μL per well) to obtain quantitative cell counts. Cytometry data were processed and analyzed using FlowJo software (BD Biosciences). Knockin efficiency was calculated as the percentage of live singlet cells expressing the BCMA-CAR construct as detected by the combination of recombinant BCMA protein (Acro Biosystems, H82E4) and anti-Myc (Cell Signaling, 9B11). Viability was calculated as the percentage of live singlet cells compared to percentage of live singlet cells in non-electroporated control. Knockin count was calculated as the total number of live singlet cells expressing the BCMA-CAR construct in 60 μL of media.

The results are shown in FIGS. 2-6. FIGS. 2A-2C demonstrate rAAV-mediated knockin and CAR and TCR flow cytometry analysis of T cells electroporated with a scramble gRNA or G526 gRNA or G526 gRNA+TRAC-CAR rAAV. FIGS. 3A-3C show ssDNA shuttle-mediated knockin. Both gRNA G526 and gRNA G527 ssDNA shuttle variants increased the maximum knockin efficiency (FIG. 3A), increased cellular viability (FIG. 3B), and increased the total number of cells recovered with the desired genetic change (FIG. 3C). Further, FIGS. 4A and 4B show enrichment of knockin by TCR-negative selection (e.g., using antibody-coated magnetic beads that target the endogenous TCR), which significantly enriched for cells with the desired knockin when guide G527 is used but not guide G526. FIGS. 6A-6D show schematic representations of CRISPR/Cas9-targeted integration into the TRAC locus using different gRNAs. Further, FIG. 6E shows representative TCR/CAR flow plots of T cells electroporation with Cas9 and TRAC gRNAs RNP and transduced with rAAV, before and after TCR negative purification.

Example 2—Comparison of Various gRNA Sequences in Their Efficiencies of Knockouts and Knockins at Various Loci Following the methods described above, gRNA sequences listed below were tested for their abilities to knockout TCR, B2M protein, or CD4 protein and knockin GFP at the TRAC locus, the B2M locus, or the CD4 locus. Activated T cells were electroporated with Cas9 and the indicated gRNA. Cell surface protein disruption was measured by flow cytometry. Genomic cutting efficiency was measured by Sanger sequencing and TIDE analysis.

Figure 7A:
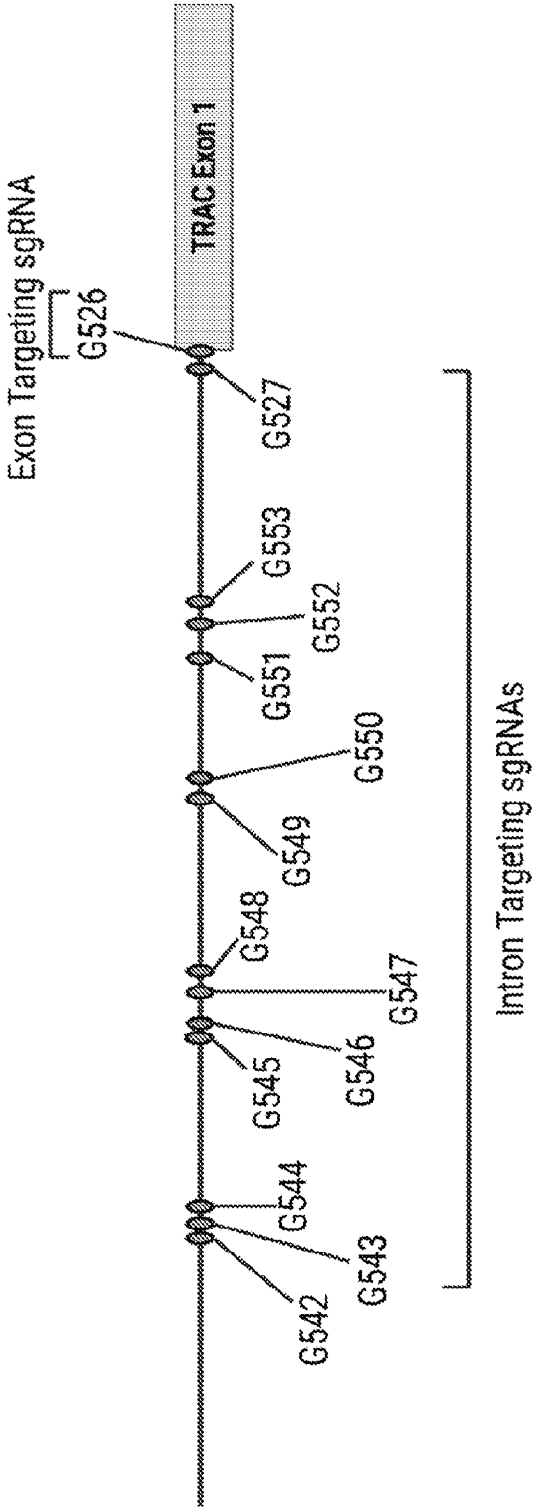
FIG. 7A shows a schematic representation of the TRAC locus and gRNAs targeting the first intron.
Figure 7B:
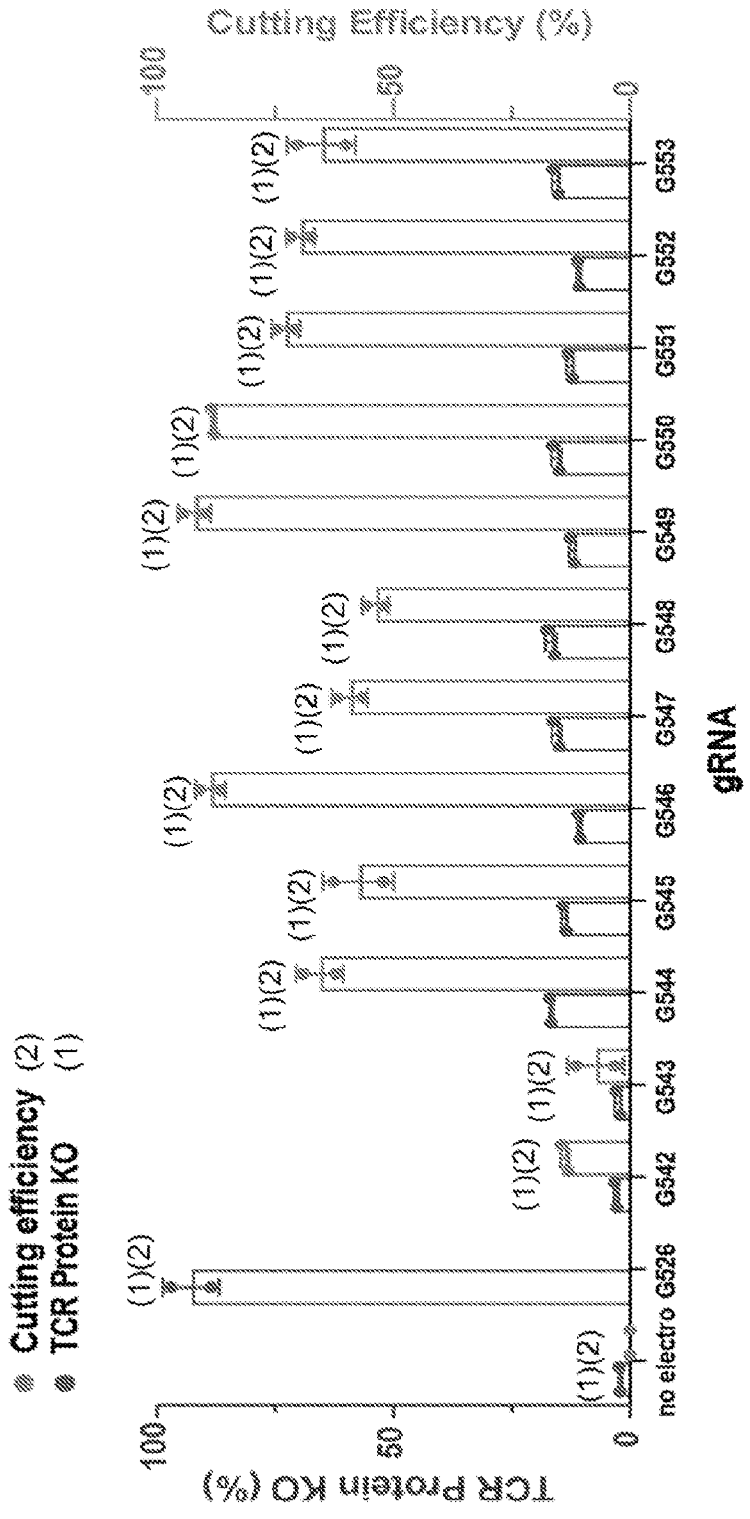
FIG. 7B shows cell surface TCR disruption as measured by flow cytometry and genomic cutting efficiency.
Figure 7C:
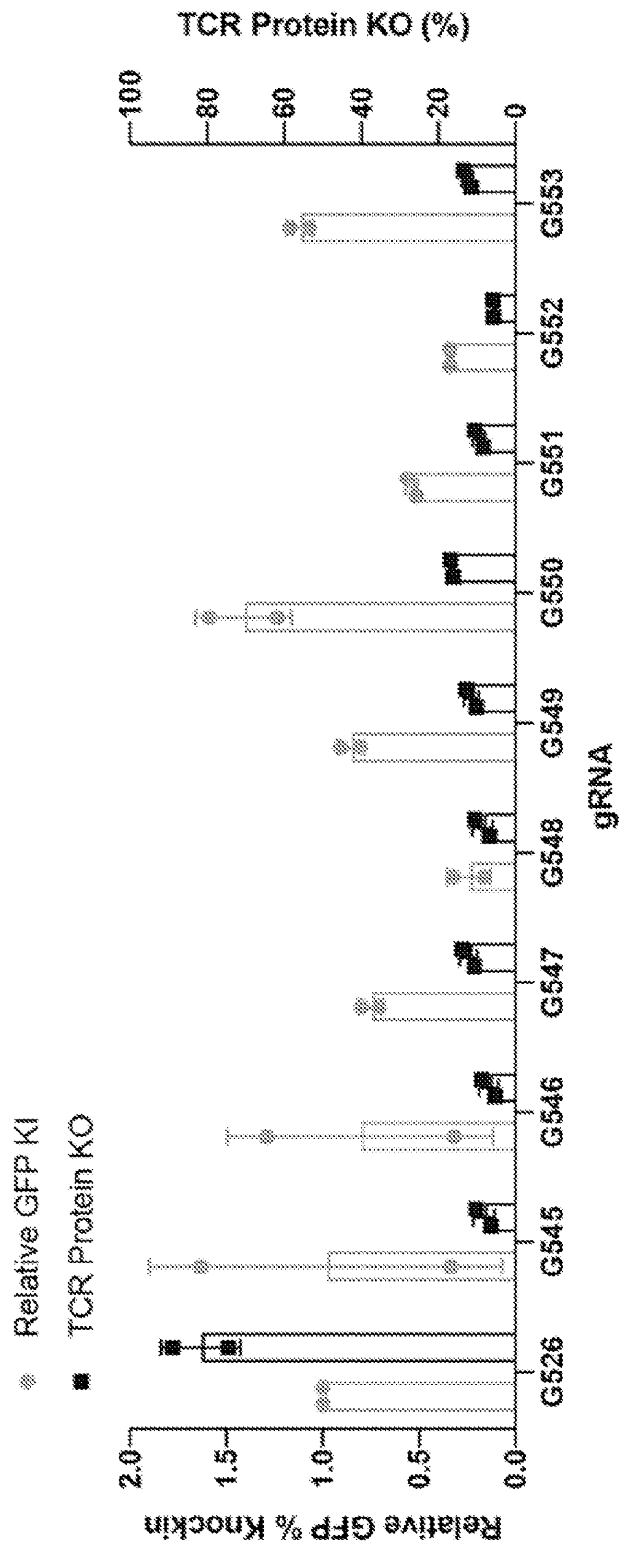
FIG. 7C shows GFP gene targeting efficiency at TRAC locus and TCR disruption with the indicated gRNA.
Figure 7D:
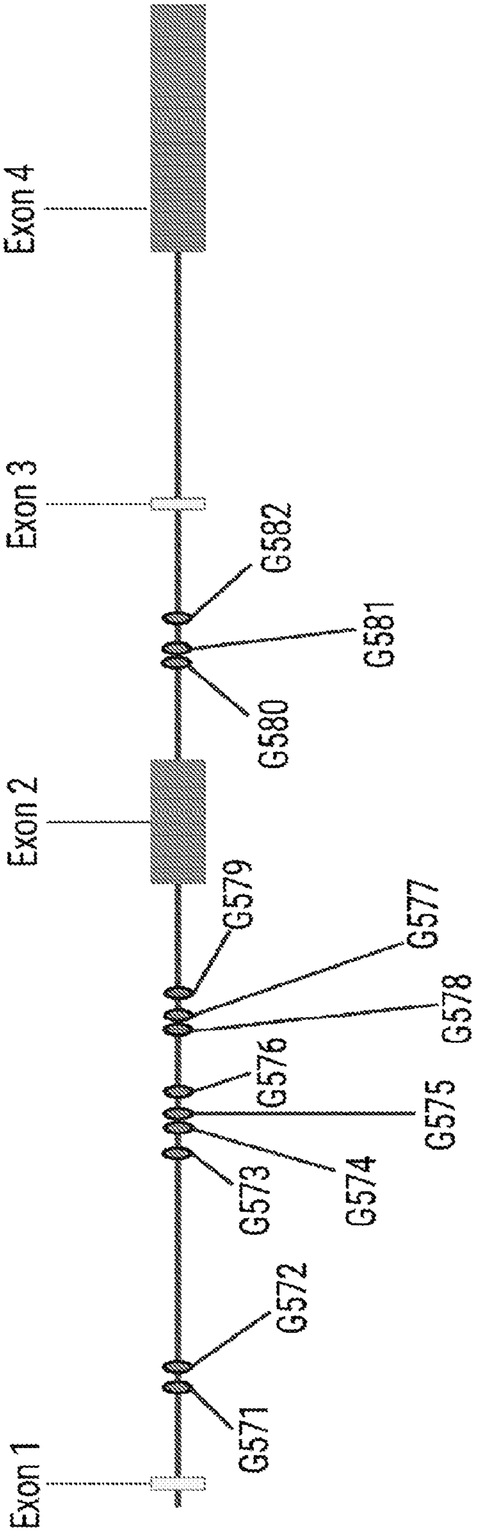
FIG. 7D shows a schematic representation of the B2M locus and gRNAs targeting the first and second introns.
Figure 7E:
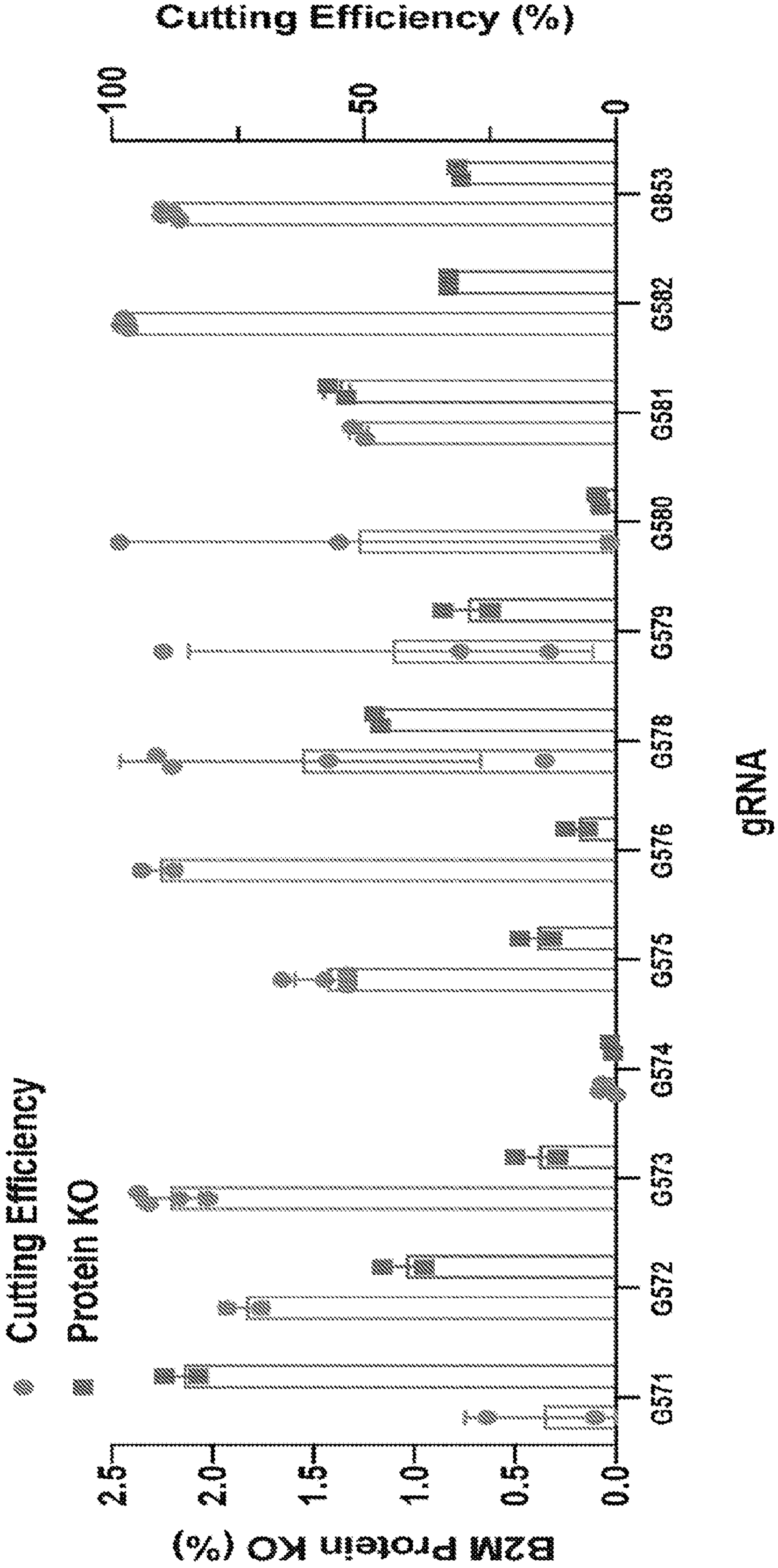
FIG. 7E shows B2M protein disruption and genomic cutting efficiency at the B2M locus.
Figure 7F:
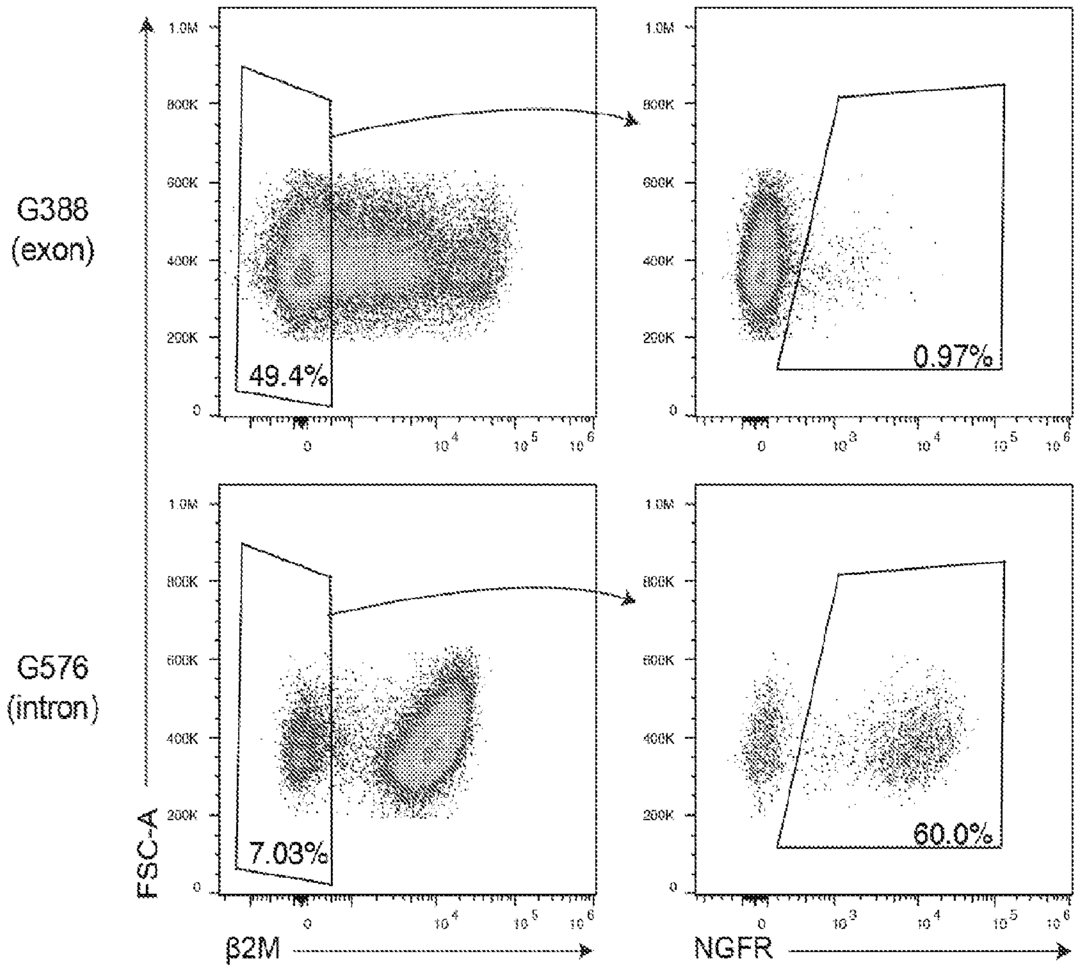
FIG. 7F shows a representative flow plot 4 days post electroporation of T cells with B2M exon or intron RNP and associated NGFR donor templates. The bottom (intron) condition shows enrichment of NGFR positive cells (KI positive) in the B2M negative cells. Thus, B2M negative selection results in an enrichment of KI positive cells.

For the TRAC locus, a schematic representation of the TRAC locus and gRNAs targeting the first intron is shown in FIG. 7A. FIG. 7B, label (1), shows cell surface TCR disruption as measured by flow cytometry. FIG. 7B, label (2), shows genomic cutting efficiency. Further, FIG. 7C shows GFP gene targeting efficiency at TRAC locus and TCR disruption with the indicated gRNA. GFP KI was measured by flow cytometry and normalized to the G526 gRNA. Cell surface TCR disruption was measured by flow cytometry For the B2M locus, a schematic representation of the B2M locus and gRNAs targeting the first and second introns is shown in FIG. 7D. Cell surface B2M disruption was measured by flow cytometry. Genomic cutting efficiency was measured by Sanger sequencing and TIDE analysis. FIG. 7E shows B2M protein disruption and genomic cutting efficiency at the B2M locus. Further, as shown in FIG. 7F, a representative flow plot 4 days post electroporation of T cells with B2M exon or intron RNP and associated NGFR donor templates demonstrates enrichment of KI positive cells after negative selection. The bottom (intron) condition shows enrichment of NGFR positive cells (KI positive) in the B2M negative cells. Thus, B2M negative selection results in an enrichment of KI positive cells.

Figure 7G:
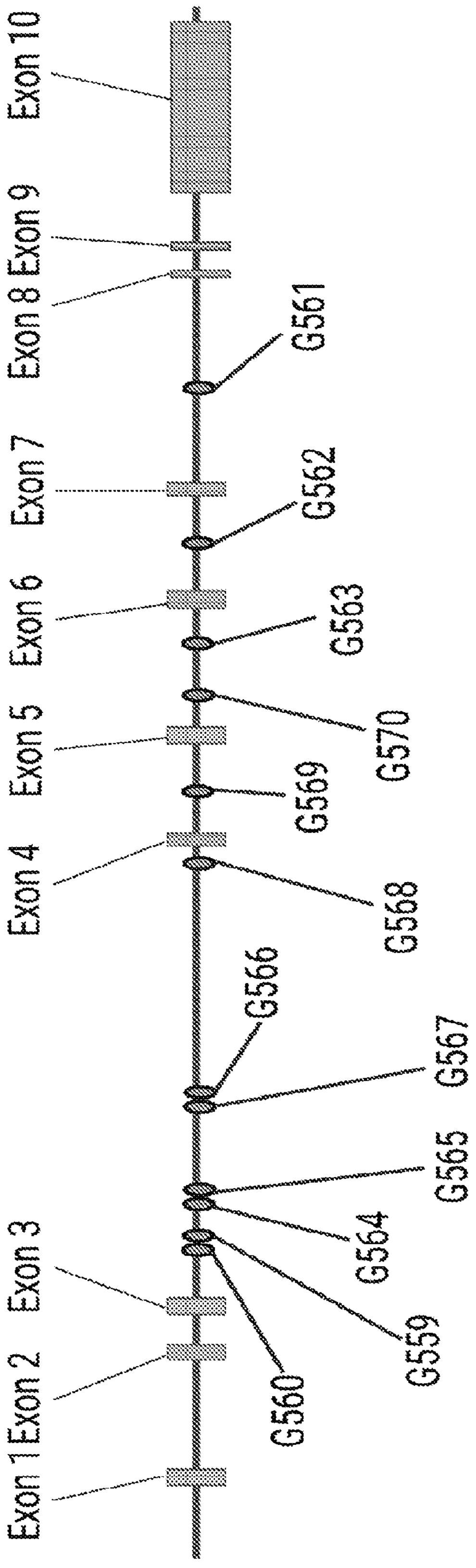
FIG. 7G shows a schematic representation of the CD4 locus and gRNAs targeting the first and second introns.

For the CD4 locus, a schematic representation of the CD4 locus and gRNAs targeting the first and second introns is shown in FIG. 7G.

TABLE 1

| SEQ ID NO | Sequence 5'-3' | Notes |
|---|---|---|
| 17 | actaccgtttactcgatataG542: | TRAC Intron Guide Optimization 1 |
| 18 | tcgagtaaacggtagtgctgG543: | TRAC Intron Guide Optimization 2 |

TABLE 1-continued

| SEQ ID NO | Sequence 5'-3' | Notes |
|---|---|---|
| 19 | tagtgctggggcttagacgcG544: | TRAC Intron Guide Optimization 3 |
| 20 | ATGGGAGGTTTATGGTATGTG545: | TRAC Intron Guide Optimization 4 |
| 21 | CTGGGCATTAGCAGAATGGGG546: | TRAC Intron Guide Optimization 5 |
| 22 | CTAATGCCCAGCCTAAGTTGG547: | TRAC Intron Guide Optimization 6 |
| 23 | GTACATCTTGGAATCTGGAGG548: | TRAC Intron Guide Optimization 7 |
| 24 | AACTCTGGCAGAGTAAAGGCG549: | TRAC Intron Guide Optimization 8 |
| 25 | CTGCCAGAGTTATATTGCTGG550: | TRAC Intron Guide Optimization 9 |
| 26 | GTGAACGTTCACTGAAATCAG551: | TRAC Intron Guide Optimization 10 |
| 27 | AGCTATCAATCTTGGCCAAGG552: | TRAC Intron Guide Optimization 11 |
| 28 | CAGGCACAAGCTATCAATCTG553: | TRAC Intron Guide Optimization 12 |
| 29 | TTTGGCCTACGGCGACGGGAG571: | B2M intron guide 1 |
| 30 | CGATAAGCGTCAGAGCGCCGG572: | B2M intron guide 2 |
| 31 | GCATGACTagaccatccatgG573: | B2M intron guide 3 |
| 32 | GTGATTGCTGTAAACTAGCCG574: | B2M intron guide 4 |
| 33 | TAGTTTACAGCAATCACCTGG575: | B2M intron guide 5 |
| 34 | ggacccgataaaatacaacaG576: | B2M intron guide 6 |
| 35 | catagcaattgctctatacgG577: | B2M intron guide 7 |
| 36 | TTCCTAAGTGGATCAACCCAG578: | B2M intron guide 8 |
| 37 | GGAATGCTATGAGTGCTGAGG579: | B2M intron guide 9 |
| 38 | GAAGCTGCCACAAAAGCTAGG580: | B2M intron guide 10 |
| 39 | ACTGAACGAACATCTCAAGAG581: | B2M intron guide 11 |
| 40 | ATTGTTTAGAGCTACCCAGCG582: | B2M intron guide 12 |
| 41 | aaggtctagttctatcacccG559: | CD4 intron guide 1 |
| 42 | tatgtataatcctagcactgG560: | CD4 intron guide 2 |
| 43 | gtacgtgtacgacagtgtgtG561: | CD4 intron guide 3 |
| 44 | AGCacttgggctaagaaccaG562: | CD4 intron guide 4 |
| 45 | tcagtcctcaacttaatacgG563: | CD4 intron guide 5 |
| 46 | agaccatcctgctagcatggG564: | CD4 intron guide 6 |
| 47 | tctcgacttcgtgatcagccG565: | CD4 intron guide 7 |
| 48 | acctgtattcccaacgacacG566: | CD4 intron guide 8 |
| 49 | tgtattcccaacgacacaggG567: | CD4 intron guide 9 |
| 50 | GGGTTTCTCTGATTAGAACGG568: | CD4 intron guide 10 |
| 51 | CATCCCTCACCTGATCAAGAG569: | CD4 intron guide 11 |
| 52 | TAAGTCACATAAGCACCCAGG570: | CD4 intron guide 12 |

Example 3—Multiple Simultaneous Intronic Knockins

Figure 10:
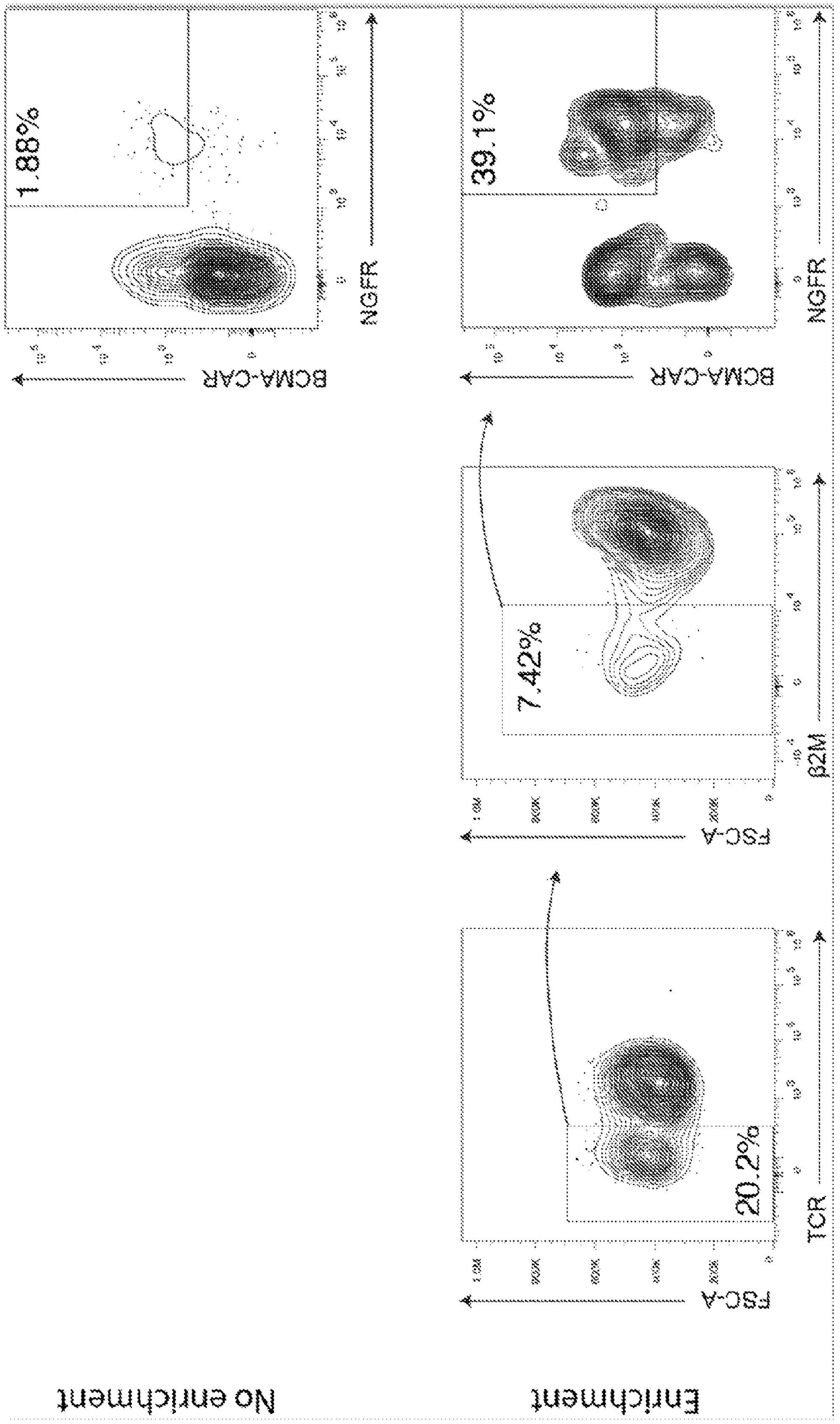
FIG. 10 shows representative flow plots of negative-selection enrichment for cells expressing both truncated-nerve growth factor receptor (NGFR) (knocked in with B2M intron targeting G576 (SEQ ID NO:34)) and a BCMA-CAR (knocked in with TRAC intron targeting G527 (SEQ ID NO:3)).

Multiple simultaneous intronic knockins were performed with B2M intron targeting G576 (SEQ ID NO:34) and with TRAC intron targeting G527 (SEQ ID NO:3). T cells were electroporated with B2M intron targeting G576 (SEQ ID NO:34) and transduced by rAAV with TRAC intron targeting G527 (SEQ ID NO:3). Truncated-nerve growth factor receptor (NGFR) was inserted into the endogenous B2M intron and a BCMA-CAR was inserted into the endogenous TRAC intron. The top condition in FIG. 10 shows double-positive cells (NGFR and BCMA-CAR positive) among live T cells before enrichment. The bottom condition in FIG. 10 shows the gating strategy to select for TCR-negative and B2M-negative live T cells via negative selections (i.e., mimics TCR and B2M-negative purification). As shown in FIG. 10, the negative selections resulted in over 20-fold enrichment of the double-positive cells (cells expressing both NGFR and BCMA-CAR) when compared to unpurified populations.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

| SEQ ID NO | Sequence | Notes |
|---|---|---|
| 1 | CTCACTAGCACTCTATCACGGCCATATTCTGGC<br>AGGGTCAGTGGCTCCAACTAACATTTGTTTGGT<br>ACTTTACAGTTTATTAAATAGATGTTTATATGG<br>AGAAGCTCTCATTTCTTTCTCAGAAGAGCCTGG<br>CTAGGAAGGTGGATGAGGCACCATATTCATTTT<br>GCAGGTGAAATTCCTGAGATGTAAGGAGCTGCT<br>GTGACTTGCTCAAGGCCTTATATCGAGTAAACG<br>GTAGTGCTGGGGCTTAGACGCAGGTGTTCTGAT<br>TTATAGTTCAAAACCTCTATCAATGAGAGAGCA<br>ATCTCCTGGTAATGTGATAGATTTCCCAACTTA<br>ATGCCAACATACCATAAACCTCCCATTCTGCTA<br>ATGCCCAGCCTAAGTTGGGGAGACCACTCCAGA<br>TTCCAAGATGTACAGTTTGCTTTGCTGGGCCTT<br>TTTCCCATGCCTGCCTTTACTCTGCCAGAGTTA<br>TATTGCTGGGGTTTTGAAGAAGATCCTATTAAA<br>TAAAAGAATAAGCAGTATTATTAAGTAGCCCTG<br>CATTTCAGGTTTCCTTGAGTGGCAGGCCAGGCC<br>TGGCCGTGAACGTTCACTGAAATCATGGCCTCT<br>TGGCCAAGATTGATAGCTTGTGCCTGTCCCTGA<br>GTCCCAGTCCATCACGAGCAGCTGGTTTCTAAG<br>ATGCTATTTCCCGTATAAAGCATGAGACCGTGA<br>CTTGCCAGCCCCACAGAGCCCCGCCCTTGTCCA<br>TCACTGGCATCTGGACTCCAGCCTGGGTTGGGG<br>CAAAGAGGGAAATGAGATCATGTCCTAACCCTG | TRAC locus |

-continued

INFORMAL SEQUENCE LISTING

| SEQ ID NO | Sequence | Notes |
|---|---|---|
| | ATCCTCTTGTCCCACAGATATCCAGAACCCTGA<br>CCCTGCCGTGTACCAGCTGAGAGACTCTAAATC<br>CAGTGACAAGTCTGTCTGCCTATTCACCGATTT<br>TGATTCTCAAACAAATGTGTCACAAAGTAAGGA<br>TTCTGATGTGTATATCACAGACAAAACTGTGCT<br>AGACATGAGGTCTATGGACTTCAAGAGCAACAG<br>TGCTGTGGCCTGGAGCAACAAATCTGACTTTGC<br>ATGTGCAAACGCCTTCAACAACAGCATTATTCC<br>AGAAGACACCTTCTTCCCCAGCCCAGGTAAGGG<br>CAGCTTTGGTGCCTTCGCAGGCTGTTTCCTTGC<br>TTCAGGAATGGCCAGGTTCTGCCCAGAGCTCTG<br>GTCAATGATGTCTAAAACTCCTCTGATTGGTGG<br>TCTCGGCCTTATCCATTGCCACCAAAACCCTCT<br>TTTTACTAAGAAACAGTGAGCCTTGTTCTGGCA<br>GTCCAGAGAATGACACGGGAAAAAAGCAGATGA<br>AGAGAAGGTGGCAGGAGAGGGCACGTGGCCCAG<br>CCTCAGTCTCTCCAACTGAGTTCCTGCCTGCCT<br>GCCTTTGCTCAGACTGTTTGCCCCTTACTGCTC<br>TTCTAGGCCTCATTCTAAGCCCCTTCTCCAAGT<br>TGCCTCTCCTTATTTCTCCCTGTCTGCCAAAAA<br>ATCTTTCCCAGCTCACTAAGTCAGTCTCACGCA<br>GTCACTCATTAACCCACCAATCACTGATTGTGC<br>CGGCACATGAATAC | |
| 2 | TCAGGGTTCTGGATATCTGT | gRNA<br>G526 |
| 3 | CTGGATATCTGTGGGACAAG | gRNA<br>G527 |
| 4 | ATCTGTGGGACAAGAGGATC | gRNA<br>G528 |
| 5 | TCTGTGGGACAAGAGGATCA | gRNA<br>G529 |
| 6 | GGGACAAGAGGATCAGGGTT | gRNA<br>G530 |
| 7 | TCTTTGCCCCAACCCAGGCT | gRNA<br>G531 |
| 8 | CTTTGCCCCAACCCAGGCTG | gRNA<br>G532 |
| 9 | TGGAGTCCAGATGCCAGTGA | gRNA<br>G533 |
| 10 | TGGCGGACCGGTTCTGGATATCTGTCGGAGCTG<br>CTGTGACTTGCTCAAGGCCTTATATCGAGTAAA<br>CGGTAGTGCTGGGGCTTAGACGCAGGTGTTCTG<br>ATTTATAGTTCAAAACCTCTATCAATGAGAGAG<br>CAATCTCCTGGTAATGTGATAGATTTCCCAACT<br>TAATGCCAACATACCATAAACCTCCCATTCTGC<br>TAATGCCCAGCCTAAGTTGGGGAGACCACTCCA<br>GATTCCAAGATGTACAGTTTGCTTTGCTGGGCC<br>TTTTTCCCATGCCTGCCTTTACTCTGCCAGAGT<br>TATATTGCTGGGGTTTTGAAGAAGATCCTATTA<br>AATAAAAGAATAAGCAGTATTATTAAGTAGCCC<br>TGCATTTCAGGTTTCCTTGAGTGGCAGGCCAGG<br>CCTGGCCGTGAACGTTCACTGAAATCATGGCCT<br>CTTGGCCAAGATTGATAGCTTGTGCCTGTCCCT<br>GAGTCCCAGTCCATCACGAGCAGCTGGTTTCTA<br>AGATGCTATTTCCCGTATAAAGCATGAGACCGT<br>GACTTGCCAGCCCCACAGAGCCCCGCCCTTGTC<br>CATCACTGGCATCTGGACTCCAGCCTGGGTTGG<br>GGCAAAGAGGGAAATGAGATCATGTCCTAACCC<br>TGGAATTGGATCCTCTTGTCTTACAGATGGATC<br>TGGAGCAACAAACTTCTCACTACTCAAACAAGC<br>AGGTGACGTGGAGGAGAATCCCGGCCCCATGGC<br>ACTTCCAGTAACTGCGCTGCTGCTCCCGCTCGC<br>ACTCCTGCTGCATGCGGCCCGACCAGAACAGAA<br>GCTTATCTCTGAAGAGGATCTTCAGGTCCAACT | HDRT-<br>733:<br>TRAC-<br>BCMA-<br>CAR<br>G526<br>ssDNA<br>shuttle |
| | CGTTCAGTCCGGCGCGGAAGTAAAAAAACCTGG<br>AGCGTCAGTTAAAGTATCCTGTAAGGCGAGTGG<br>ATATTCATTTCCCGATTATTACATTAATTGGGT<br>GCGACAAGCGCCTGGTCAGGGTCTTGAATGGAT<br>GGGATGGATATACTTCGCGTCTGGGAATAGTGA<br>ATACAATCAGAAATTTACCGGCAGGGTGACGAT<br>GACGCGAGACACCTCCATTAATACTGCCTATAT<br>GGAACTCAGCTCTCTCACTTCAGAGGACACAGC<br>CGTCTACTTCTGTGCCTCCCTTTATGATTACGA<br>TTGGTATTTTGACGTGTGGGGTCAAGGAACTAT<br>GGTTACTGTGTCTAGCGGGGGAGGTGGCTCAGG<br>TGGGGGAGGTTCAGGAGGAGGCGGGTCCGACAT<br>CGTGATGACACAAACCCCTCTGAGCCTGAGCGT<br>TACGCCAGGGCAACCAGCCTCCATTTCATGCAA<br>GTCCAGCCAGTCACTCGTGCATTCAAATGGAAA<br>CACCTATCTGCACTGGTATCTTCAAAAACCAGG<br>TCAGTCACCCCAGTTGTTGATATACAAAGTTAG<br>TAATCGCTTCTCCGGAGTACCCGATCGGTTCAG<br>CGGGTCTGGTTCAGGGACGGATTTCACCTTGAA<br>AATTAGCCGAGTTGAGGCTGAAGATGTGGGAAT<br>TTACTATTGCAGTCAGAGCAGCATTTACCCCTG<br>GACGTTCGGGCAGGGCACCAAGTTGGAAATTAA<br>GGCGGCCGCAATTGAAGTTATGTATCCTCCTCC<br>TTACCTAGACAATGAGAAGAGCAATGGAACCAT<br>TATCCATGTGAAAGGGAAACACCTTTGTCCAAG<br>TCCCCTATTTCCCGGACCTTCTAAGCCCTTTTG<br>GGTGCTGGTGGTGGTTGGTGGAGTCCTGGCTTG<br>CTATAGCTTGCTAGTAACAGTGGCCTTTATTAT<br>TTTCTGGGTGAGGAGTAAGAGGAGCAGGCTCCT<br>GCACAGTGACTACATGAACATGACTCCCCGCCG<br>CCCCGGGCCCACCCGCAAGCATTACCAGCCCTA<br>TGCCCCACCACGCGACTTCGCAGCCTATCGCTC<br>CAGAGTGAAGTTCAGCAGGAGCGCAGACGCCCC<br>CGCGTACCAGCAGGGCCAGAACCAGCTCTATAA<br>CGAGCTCAATCTAGGACGAAGAGAGGAGTACGA<br>TGTTTTGGACAAGAGACGTGGCCGGGACCCTGA<br>GATGGGGGGAAAGCCGAGAAGGAAGAACCCTCA<br>GGAAGGCCTGTACAATGAACTGCAGAAAGATAA<br>GATGGCGGAGGCCTACAGTGAGATTGGGATGAA<br>AGGCGAGCGCCGGAGGGGCAAGGGGCACGATGG<br>CCTTTACCAGGGTCTCAGTACAGCCACCAAGGA<br>CACCTACGACGCCCTTCACATGCAGGCCCTGCC<br>CCCTCGCGGAAGCGGAGCTACTAACTTCAGCCT<br>GCTGAAGCAGGCTGGAGACGTGGAGGAGAACCC<br>TGGACCCAATATCCAGAACCCTGACCCTGCCGT<br>GTACCAGCTGAGAGACTCTAAATCCAGTGACAA<br>GTCTGTCTGCCTATTCACCGATTTTGATTCTCA<br>AACAAATGTGTCACAAAGTAAGGATTCTGATGT<br>GTATATCACAGACAAAACTGTGCTAGACATGAG<br>GTCTATGGACTTCAAGAGCAACAGTGCTGTGGC<br>CTGGAGCAACAAATCTGACTTTGCATGTGCAAA<br>CGCCTTCAACAACAGCATTATTCCAGAAGACAC<br>CTTCTTCCCCAGCCCAGGTAAGGGCAGCTTTGG<br>TGCCTTCGCAGGCTGTTTCCTTGCTTCAGGAAT<br>GGCCAGGTTCTGCCCAGAGCTCTGGTCAATGAT<br>GTCTAAAACTCCTCTGATTGGTGGTCTCGGCCT<br>TATCCATTGCCACCAAAACCCTCTTTTTACTAA<br>GAAACAGTGAGCCTTGTTCTGGCAGTCCAGAGA<br>ATGACACGGGAAAAAAGCAGATGAAGAGAAGGT<br>GGCAGGAGAGGGCACGTGGCCCAGCCTCAGTCT<br>CTCCAACTGAGTTCCTGCCTGCCTGCCTTTGCT<br>CAGACTGTTTGCCCCTTACTGCTCTTCTAGGCC<br>TCATTCTAAGCCCCTTCTCCAAGTCCTACAGAT<br>ATCCAGAACCGAGATGGTG | |
| 11 | TGGCGGACCATATCTGTGGGACAAGCGGAGCTG<br>CTGTGACTTGCTCAAGGCCTTATATCGAGTAAA<br>CGGTAGTGCTGGGGCTTAGACGCAGGTGTTCTG<br>ATTTATAGTTCAAAACCTCTATCAATGAGAGAG<br>CAATCTCCTGGTAATGTGATAGATTTCCCAACT<br>TAATGCCAACATACCATAAACCTCCCATTCTGC<br>TAATGCCCAGCCTAAGTTGGGGAGACCACTCCA<br>GATTCCAAGATGTACAGTTTGCTTTGCTGGGCC | HDRT-<br>734:<br>TRAC-<br>BCMA-<br>CAR<br>G527<br>ssDNA<br>shuttle |

-continued

INFORMAL SEQUENCE LISTING

| SEQ ID NO | Sequence | Notes |
|---|---|---|
| | TTTTTCCCATGCCTGCCTTTACTCTGCCAGAGT<br>TATATTGCTGGGGTTTTGAAGAAGATCCTATTA<br>AATAAAAGAATAAGCAGTATTATTAAGTAGCCC<br>TGCATTTCAGGTTTCCTTGAGTGGCAGGCCAGG<br>CCTGGCCGTGAACGTTCACTGAAATCATGGCCT<br>CTTGGCCAAGATTGATAGCTTGTGCCTGTCCCT<br>GAGTCCCAGTCCATCACGAGCAGCTGGTTTCTA<br>AGATGCTATTTCCCGTATAAAGCATGAGACCGT<br>GACTTGCCAGCCCCACAGAGCCCCGCCCTTGTC<br>CATCACTGGCATCTGGACTCCAGCCTGGGTTGG<br>GGCAAAGAGGGAAATGAGATCATGTCCTAACCC<br>TGGAATTGGATCCTCTTGTCTTACAGATGGATC<br>TGGAGCAACAAACTTCTCACTACTCAAACAAGC<br>AGGTGACGTGGAGGAGAATCCCGGCCCCATGGC<br>ACTTCCAGTAACTGCGCTGCTGCTCCCGCTCGC<br>ACTCCTGCTGCATGCGGCCCGACCAGAACAGAA<br>GCTTATCTCTGAAGAGGATCTTCAGGTCCAACT<br>CGTTCAGTCCGGCGCGGAAGTAAAAAAACCTGG<br>AGCGTCAGTTAAAGTATCCTGTAAGGCGAGTGG<br>ATATTCATTTCCCGATTATTACATTAATTGGGT<br>GCGACAAGCGCCTGGTCAGGGTCTTGAATGGAT<br>GGGATGGATATACTTCGCGTCTGGGAATAGTGA<br>ATACAATCAGAAATTTACCGGCAGGGTGACGAT<br>GACGCGAGACACCTCCATTAATACTGCCTATAT<br>GGAACTCAGCTCTCTCACTTCAGAGGACACAGC<br>CGTCTACTTCTGTGCCTCCCTTTATGATTACGA<br>TTGGTATTTTGACGTGTGGGGTCAAGGAACTAT<br>GGTTACTGTGTCTAGCGGGGGAGGTGGCTCAGG<br>TGGGGGAGGTTCAGGAGGAGGCGGGTCCGACAT<br>CGTGATGACACAAACCCCTCTGAGCCTGAGCGT<br>TACGCCAGGGCAACCAGCCTCCATTTCATGCAA<br>GTCCAGCCAGTCACTCGTGCATTCAAATGGAAA<br>CACCTATCTGCACTGGTATCTTCAAAAACCAGG<br>TCAGTCACCCCAGTTGTTGATATACAAAGTTAG<br>TAATCGCTTCTCCGGAGTACCCGATCGGTTCAG<br>CGGGTCTGGTTCAGGGACGGATTTCACCTTGAA<br>AATTAGCCGAGTTGAGGCTGAAGATGTGGGAAT<br>TTACTATTGCAGTCAGAGCAGCATTTACCCCTG<br>GACGTTCGGGCAGGGCACCAAGTTGGAAATTAA<br>GGCGGCCGCAATTGAAGTTATGTATCCTCCTCC<br>TTACCTAGACAATGAGAAGAGCAATGGAACCAT<br>TATCCATGTGAAAGGGAAACACCTTTGTCCAAG<br>TCCCCTATTTCCCGGACCTTCTAAGCCCTTTTG<br>GGTGCTGGTGGTGGTTGGTGGAGTCCTGGCTTG<br>CTATAGCTTGCTAGTAACAGTGGCCTTTATTAT<br>TTTCTGGGTGAGGAGTAAGAGGAGCAGGCTCCT<br>GCACAGTGACTACATGAACATGACTCCCCGCCG<br>CCCCGGGCCCACCCGCAAGCATTACCAGCCCTA<br>TGCCCCACCACGCGACTTCGCAGCCTATCGCTC<br>CAGAGTGAAGTTCAGCAGGAGCGCAGACGCCCC<br>CGCGTACCAGCAGGGCCAGAACCAGCTCTATAA<br>CGAGCTCAATCTAGGACGAAGAGAGGAGTACGA<br>TGTTTTGGACAAGAGACGTGGCCGGGACCCTGA<br>GATGGGGGGAAAGCCGAGAAGGAAGAACCCTCA<br>GGAAGGCCTGTACAATGAACTGCAGAAAGATAA<br>GATGGCGGAGGCCTACAGTGAGATTGGGATGAA<br>AGGCGAGCGCCGGAGGGGCAAGGGGCACGATGG<br>CCTTTACCAGGGTCTCAGTACAGCCACCAAGGA<br>CACCTACGACGCCCTTCACATGCAGGCCCTGCC<br>CCCTCGCGGAAGCGGAGCTACTAACTTCAGCCT<br>GCTGAAGCAGGCTGGAGACGTGGAGGAGAACCC<br>TGGACCCAATATCCAGAACCCTGACCCTGCCGT<br>GTACCAGCTGAGAGACTCTAAATCCAGTGACAA<br>GTCTGTCTGCCTATTCACCGATTTTGATTCTCA<br>AACAAATGTGTCACAAAGTAAGGATTCTGATGT<br>GTATATCACAGACAAAACTGTGCTAGACATGAG<br>GTCTATGGACTTCAAGAGCAACAGTGCTGTGGC<br>CTGGAGCAACAAATCTGACTTTGCATGTGCAAA<br>CGCCTTCAACAACAGCATTATTCCAGAAGACAC<br>CTTCTTCCCCAGCCCAGGTAAGGGCAGCTTTGG<br>TGCCTTCGCAGGCTGTTTCCTTGCTTCAGGAAT<br>GGCCAGGTTCTGCCCAGAGCTCTGGTCAATGAT<br>GTCTAAAACTCCTCTGATTGGTGGTCTCGGCCT<br>TATCCATTGCCACCAAAACCCTCTTTTTACTAA<br>GAAACAGTGAGCCTTGTTCTGGCAGTCCAGAGA<br>ATGACACGGGAAAAAAGCAGATGAAGAGAAGGT<br>GGCAGGAGAGGGCACGTGGCCCAGCCTCAGTCT<br>CTCCAACTGAGTTCCTGCCTGCCTGCCTTTGCT<br>CAGACTGTTTGCCCCTTACTGCTCTTCTAGGCC<br>TCATTCTAAGCCCCTTCTCCAAGTCCTCTTGTC<br>CCACAGATATGAGATGGTG | |
| 12 | AVKRPAATKKAGQAKKKKLD | NLS se-quence |
| 13 | MSRRRKANPTKLSENAKKLAKEVEN | NLS se-quence |
| 14 | PAAKRVKLD | NLS se-quence |
| 15 | KLKIKRPVK | NLS se-quence |
| 16 | PKKKRKV | NLS se-quence |

What is claimed is:

1. A method for modifying an endogenous T cell receptor alpha constant chain (TRAC) genomic locus in a T cell with at least two chimeric antigen receptors (CARs), the method comprising the step of introducing into the T cell:

i) a guide RNA (gRNA) comprising the sequence of CTGGATATCTGTGGGACAAG (SEQ ID NO:3), ATCTGTGGGACAAGAGGATC (SEQ ID NO:4), TCTGTGGGACAAGAGGATCA (SEQ ID NO:5), GGGACAAGAGGATCAGGGTT (SEQ ID NO:6), TCTTTGCCCCAACCCAGGCT (SEQ ID NO:7), CTTTGCCCCAACCCAGGCTG (SEQ ID NO:8), TGGAGTCCAGATGCCAGTGA (SEQ ID NO:9), ACTACCGTTTACTCGATATA (SEQ ID NO: 17), TCGAGTAAACGGTAGTGCTG (SEQ ID NO: 18), TAGTGCTGGGGCTTAGACGC (SEQ ID NO: 19), ATGGGAGGTTTATGGTATGT (SEQ ID NO:20), CTGGGCATTAGCAGAATGGG (SEQ ID NO:21), CTAATGCCCAGCCTAAGTTG (SEQ ID NO:22), GTACATCTTGGAATCTGGAG (SEQ ID NO:23), AACTCTGGCAGAGTAAAGGC (SEQ ID NO:24), CTGCCAGAGTTATATTGCTG (SEQ ID NO:25), GTGAACGTTCACTGAAATCA (SEQ ID NO:26), AGCTATCAATCTTGGCCAAG (SEQ ID NO:27), or CAGGCACAAGCTATCAATCT (SEQ ID NO:28);

ii) a homology-directed repair template (HDRT) comprising a sequence having at least 95% identity to the sequence of SEQ ID NO:10 or 11 encoding the at least two CARs; and iii) a Cas protein, thereby integrating the nucleotide sequence encoding the at least two CARs into the endogenous TRAC locus of the T cell.

2. The method of claim 1, wherein the introducing comprises electroporation or viral delivery.

3. The method of claim 1, further comprising selecting for T cells that do not express the endogenous TRAC protein.

4. A composition comprising:

i) a guide RNA (gRNA) comprising the sequence of CTGGATATCTGTGGGACAAG (SEQ ID NO:3), ATCTGTGGGACAAGAGGATC (SEQ ID NO:4), TCTGTGGGACAAGAGGATCA (SEQ ID NO:5), GGGACAAGAGGATCAGGGTT (SEQ ID NO:6), TCTTTGCCCCAACCCAGGCT (SEQ ID NO:7), CTTTGCCCCAACCCAGGCTG (SEQ ID NO:8), TGGAGTCCAGATGCCAGTGA (SEQ ID NO:9), ACTACCGTTTACTCGATATA (SEQ ID NO: 17), TCGAGTAAACGGTAGTGCTG (SEQ ID NO: 18), TAGTGCTGGGGCTTAGACGC (SEQ ID NO: 19), ATGGGAGGTTTATGGTATGT (SEQ ID NO:20), CTGGGCATTAGCAGAATGGG (SEQ ID NO:21), CTAATGCCCAGCCTAAGTTG (SEQ ID NO:22), GTACATCTTGGAATCTGGAG (SEQ ID NO:23), AACTCTGGCAGAGTAAAGGC (SEQ ID NO:24), CTGCCAGAGTTATATTGCTG (SEQ ID NO:25), GTGAACGTTCACTGAAATCA (SEQ ID NO:26), AGCTATCAATCTTGGCCAAG (SEQ ID NO:27), or CAGGCACAAGCTATCAATCT (SEQ ID NO:28); and ii) a homology-directed repair template (HDRT) comprising a sequence having at least 95% identity to the sequence of SEQ ID NO:10 or 11.

5. The composition of claim 4, further comprising a Cas protein.

6. The composition of claim 4, wherein the HDRT comprises the sequence of SEQ ID NO: 10 or 11.

7. The composition of claim 4, wherein the compositions comprises an anionic polymer.

* * * * *